US006872533B2

(12) United States Patent
Toland et al.

(10) Patent No.: US 6,872,533 B2
(45) Date of Patent: Mar. 29, 2005

(54) STK15 (STK6) GENE POLYMORPHISM AND METHODS OF DETERMINING CANCER RISK

(75) Inventors: Amanda E. Toland, Greenbrae, CA (US); Allan Balmain, Tiburon, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/209,324

(22) Filed: Jul. 29, 2002

(65) Prior Publication Data

US 2003/0108910 A1 Jun. 12, 2003

Related U.S. Application Data

(60) Provisional application No. 60/308,911, filed on Jul. 27, 2001, and provisional application No. 60/334,146, filed on Nov. 28, 2001.

(51) Int. Cl.[7] ............................ C12Q 1/68; C12P 19/34; C07H 21/02; C07H 21/04
(52) U.S. Cl. ........................ 435/6; 435/91.2; 536/23.5; 536/24.31; 536/24.33
(58) Field of Search .................. 435/6, 91.2; 536/23.5, 536/24.31, 24.33

(56) References Cited

U.S. PATENT DOCUMENTS 5,962,312 A 10/1999 Plowman et al.

OTHER PUBLICATIONS

Cluster Report, dbsnp, rs2273535, Sep. 5, 2001.
Bischoff and Plowman, "The Aurora/Ip11p Kinase Family: Regulators of Chromosome Segregation and Cytokinesis," *Cell Biology*, 9, 454–459 (1999).
Bischoff, J., et al., "A Homologue of *Drosophilia Aurora* Kinase is Oncogenic and Amplified in Human Colorectal Cancers," *EMBO J.*, 17(11), 3052–3065 (1998).
Cluster Report, dbsnp, rs2273535, Sep. 5, 1991.
Iwabuchi, et al., "Genetic Analysis of Benign, Low–Grade, and High–Grade Ovarian Tumors," *Cancer Research*, 55, 6172–6180, (1999).
Kallioniemi, A., et al., "Detection and Mapping of Amplified DNA Sequences in Breast Cancer by Comparative Genomic Hybridization," *PNAS*, 91, 2156–2160 (1994).
Kimura, M., et al., "Cell Cycle–dependent Expression and Spindle Pole Localization of a Novel Human Protein Kinase, Aik, Related to Aurora of *Drosophila* and Yeast Ip11," *J. Biol. Chem.*, 272(21), 13766–13771 (1997).

Korn, W.M., et al., "Chromosome Arm 20q Gains and Other Genomic Alterations in Colorectal Cancer Metastatic to Liver, as Analyzed by Comparative Genomic Hybridization and Fluorescence in Situ Hybridization," *Genes, Chromosomes & Cancer*, 25, 82–90 (1999).
Miyoshi, Y., et al., "Association of Centrosomal Kinase STK15/BTAK MRNA Expression with Chromosomal Instability in Human Breast Cancers," *Int. J. Cancer*, 92, 370–373 (2001).
Nagase, H., et al., "A Subset of Skin Tumor Modifier Loci Determines Survival Time of Tumor–Bearing Mice," *PNAS*, v. 96(26) 15032–15037 (1999).
OMIM, 603072, Sep. 29, 1998.
Romanov, S., et al., "Normal Human Mammary Epithelial Cells Spontaneously Escape Senescence and Acquire Genomic Changes," *Nature*, 409, 633–637 (2001).
Sen, S., et al., "A Putative Serine/Threonine Kinase Encoding Gene *BTAK* on Chromosome 20q13 is amplified and Overexpressed in Human Breast Cancer Cell Lines," *Oncogene*, 14, 2195–2200 (1997).
Sequence ID No.: NM_003600 [gi:4507274], Apr. 10, 2002.
Sequence ID No.: NM_003158 [gi:4507278], Oct., 31, 2000.
Tanaka, T, et al., "Centrosomal Kinase AIK1 is Overexpressed in Invasive Ductal Carcinoma of the Breast," *Cancer Research*, 59, 2041–2044 (1999).
Tanner, M., et al., "Frequent Amplification of Chromosomal Region 20q12–q13 in Ovarian Cancer," *Clinical Cancer Research*, 6, 1833–1839 (2000).
Zhou, H., et al., "Tumour Amplified Kinase *STK15/BTAK* Induces Centrosome Amplification, Aneuploidy and Transformation," *Nature Genetics*, 20, 189–193 (1998).
Wang, et al., "Analysis of the STK15 Gene in Familial and Sporadic Prostate Cancer"; Proceedings of the American Association for Cancer Research, Mar. 2002, vol. 43, p. 929.

*Primary Examiner*—Carla J. Myers
(74) *Attorney, Agent, or Firm*—Gray Cary Ware & Freidenrich, LLP

(57) ABSTRACT

The present invention provides methods for determining cancer susceptibility in a human subject by identifying in a nucleic acid sample from the subject, a nucleotide occurrence of a single nucleotide polymorphism (SNP) of the STK15 gene, including the STK15 Ile31 polymorphism. The invention provides isolated polynucleotides, polypeptides, specific binding pair members, and cells useful for identifying agents that affect tumor susceptibility. Furthermore, the invention provides methods for detecting low penetrance tumor susceptibility genes.

16 Claims, 7 Drawing Sheets

SEQUENCE LISTING

```
<160> NUMBER OF SEQ ID NOS: 34

<210> SEQ ID NO 1
<211> LENGTH: 2347
<212> TYPE: DNA
<213> ORGANISM: Homo sapiens
<220> FEATURE:
<221> NAME/KEY: misc_feature
<222> LOCATION: (457)..(457)
<223> OTHER INFORMATION: n = t or a

<400> SEQUENCE: 1
ggaagacttg ggtccttggg tcgcaggtgg gagccgacgg gtgggtagac cgtgggggat     60
atctcagtgg cggacgagga cggcggggac aagggggcggc tggtcggagt ggcggagcgt    120
caagtcccct gtcggttcct ccgtccctga gtgtccttgg cgctgccttg tgcccgccca    180
gcgcctttgc atccgctcct gggcaccgag gcgccctgta ggatactgct tgttacttat    240
tacagctaga gggtctcact ccattgccca ggccagagtg cggggatatt tgataagaaa    300
cttcagtgaa ggccgggcgc ggtggctcat gcccgtaatc ccagcatttt cggaggccga    360
ggcatcatgg accgatctaa agaaaactgc atttcaggac ctgttaaggc tacagctcca    420
gttggaggtc caaaacgtgt tctcgtgact cagcaaattc cttgtcagaa tccattacct    480
gtaaatagtg gccaggctca gcgggtcttg tgtccttcaa attcttccca gcgcattcct    540
ttgcaagcac aaaagcttgt ctccagtcac aagccggttc agaatcagaa gcagaagcaa    600
ttgcaggcaa ccagtgtacc tcatcctgtc tccaggccac tgaataacac ccaaaagagc    660
aagcagcccc tgccatcggc acctgaaaat aatcctgagg aggaactggc atcaaaacag    720
```

-continued

```
aaaaatgaag aatcaaaaaa gaggcagtgg gctttggaag actttgaaat tggtcgccct    780
ctgggtaaag gaaagtttgg taatgtttat ttggcaagag aaaagcaaag caagtttatt    840
ctggctctta aagtgttatt taaagctcag ctggagaaaa ccggagtgga gcatcagctc    900
agaagagaag tagaaataca gtcccacctt cggcatccta atattcttag actgtatggt    960
tatttccatg atgctaccag agtctaccta attctggaat atgcaccact tggaacagtt   1020
tatagagaac ttcagaaact ttcaaagttt gatgagcaga aactgctac ttatataaca    1080
gaattggcaa atgccctgtc ttactgtcat tcgaagagag ttattcatag agacattaag   1140
ccagagaact tacttcttgg atcagctgga gagcttaaaa ttgcagattt tgggtggtca   1200
gtacatgctc catcttccag gaggaccact ctctgtggca ccctggacta cctgccccct   1260
gaaatgattg aaggtcggat gcatgatgag aaggtggatc tctggagcct tggagttctt   1320
tgctatgaat ttttagttgg gaagcctcct tttgaggcaa acacatacca agagacctac   1380
aaaagaatat cacgggttga attcacattc cctgactttg taacagaggg agccagggac   1440
ctcatttcaa gactgttgaa gcataatccc agccagaggc caatgctcag agaagtactt   1500
gaacacccct ggatcacagc aaattcatca aaaccatcaa attgccaaaa caagaatca    1560
gctagcaaac agtcttagga atcgtgcagg gggagaaatc cttgagccag gctgccata    1620
taacctgaca ggaacatgct actgaagttt attttaccat tgactgctgc cctcaatcta   1680
gaacgctaca caagaaatat ttgtttact cagcaggtgt gccttaacct ccctattcag    1740
aaagctccac atcaataaac atgacactct gaagtgaaaa tagccacgag aattgtgcta   1800
cttatactgg ttcataatct ggaggcaagg ttcgactgca gccgccccgt cagcctgtgc   1860
taggcatggt gtcttcacag gaggcaaatc cagagcctgg ctgtggggaa agtgaccact   1920
ctgccctgac cccgatcagt taaggagctg tgcaataacc ttcctagtac ctgagtgagt   1980
gtgtaactta ttgggttggc gaagcctggt aaagctgttg gaatgagtat gtgattcttt   2040
ttaagtatga aaataaagat atatgtacag acttgtattt tttctctggt ggcattcctt   2100
taggaatgct gtgtgtctgt ccggcacccc ggtaggcctg attgggtttc tagtcctcct   2160
taaccactta tctcccatat gagagtgtga aaaataggaa cacgtgctct acctccattt   2220
agggatttgc ttgggataca gaagaggcca tgtgtctcag agctgttaag ggcttatttt   2280
tttaaaacat tggagtcata gcatgtgtgt aaactttaaa tatgcaaata aataagtatc   2340
tatgtct                                                              2347
```

<210> SEQ ID NO 2
<211> LENGTH: 403
<212> TYPE: PRT
<213> ORGANISM: Homo sapiens
<220> FEATURE:
<221> NAME/KEY: MISC_FEATURE
<222> LOCATION: (31)..(31)
<223> OTHER INFORMATION: Xaa is Ile or Phe

<400> SEQUENCE: 2

```
Met Asp Arg Ser Lys Glu Asn Cys Ile Ser Gly Pro Val Lys Ala Thr
 1               5                  10                  15

Ala Pro Val Gly Gly Pro Lys Arg Val Leu Val Thr Gln Gln Xaa Pro
                20                  25                  30

Cys Gln Asn Pro Leu Pro Val Asn Ser Gly Gln Ala Gln Arg Val Leu
            35                  40                  45

Cys Pro Ser Asn Ser Ser Gln Arg Val Pro Leu Gln Ala Gln Lys Leu
```

```
                50                  55                  60
Val Ser Ser His Lys Pro Val Gln Asn Gln Lys Gln Lys Gln Leu Gln
 65                  70                  75                  80

Ala Thr Ser Val Pro His Pro Val Ser Arg Pro Leu Asn Asn Thr Gln
                 85                  90                  95

Lys Ser Lys Gln Pro Leu Pro Ser Ala Pro Glu Asn Asn Pro Glu Glu
                100                 105                 110

Glu Leu Ala Ser Lys Gln Lys Asn Glu Glu Ser Lys Lys Arg Gln Trp
                115                 120                 125

Ala Leu Glu Asp Phe Glu Ile Gly Arg Pro Leu Gly Lys Gly Lys Phe
                130                 135                 140

Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
                165                 170                 175

Gln Leu Arg Arg Glu Val Glu Ile Gln Ser His Leu Arg His Pro Asn
                180                 185                 190

Ile Leu Arg Leu Tyr Gly Tyr Phe His Asp Ala Thr Arg Val Tyr Leu
                195                 200                 205

Ile Leu Glu Tyr Ala Pro Leu Gly Thr Val Tyr Arg Glu Leu Gln Lys
210                 215                 220

Leu Ser Lys Phe Asp Glu Gln Arg Thr Ala Thr Tyr Ile Thr Glu Leu
225                 230                 235                 240

Ala Asn Ala Leu Ser Tyr Cys His Ser Lys Arg Val Ile His Arg Asp
                245                 250                 255

Ile Lys Pro Glu Asn Leu Leu Leu Gly Ser Ala Gly Glu Leu Lys Ile
                260                 265                 270

Ala Asp Phe Gly Trp Ser Val His Ala Pro Ser Ser Arg Arg Thr Thr
                275                 280                 285

Leu Cys Gly Thr Leu Asp Tyr Leu Pro Pro Glu Met Ile Glu Gly Arg
                290                 295                 300

Met His Asp Glu Lys Val Asp Leu Trp Ser Leu Gly Val Leu Cys Tyr
305                 310                 315                 320

Glu Phe Leu Val Gly Lys Pro Pro Phe Glu Ala Asn Thr Tyr Gln Glu
                325                 330                 335

Thr Tyr Lys Arg Ile Ser Arg Val Glu Phe Thr Phe Pro Asp Phe Val
                340                 345                 350

Thr Glu Gly Ala Arg Asp Leu Ile Ser Arg Leu Leu Lys His Asn Pro
                355                 360                 365

Ser Gln Arg Pro Met Leu Arg Glu Val Leu Glu His Pro Trp Ile Thr
                370                 375                 380

Ala Asn Ser Ser Lys Pro Ser Asn Cys Gln Asn Lys Glu Ser Ala Ser
385                 390                 395                 400

Lys Gln Ser

<210> SEQ ID NO 3
<211> LENGTH: 21
<212> TYPE: DNA
<213> ORGANISM: Artificial sequence
<220> FEATURE:
<223> OTHER INFORMATION: Amplification reaction primer

<400> SEQUENCE: 3
ctgttgcagc agagggctta g                                           21
```

```
<210> SEQ ID NO 4
<211> LENGTH: 21
<212> TYPE: DNA
<213> ORGANISM: Artificial sequence
<220> FEATURE:
<223> OTHER INFORMATION: Amplification reaction primer

<400> SEQUENCE: 4
cagcaaggag gtagccacag a                                      21

<210> SEQ ID NO 5
<211> LENGTH: 19
<212> TYPE: DNA
<213> ORGANISM: Artificial sequence
<220> FEATURE:
<223> OTHER INFORMATION: Probe sequence

<400> SEQUENCE: 5
atgcccatct gttacatat                                         19

<210> SEQ ID NO 6
<211> LENGTH: 19
<212> TYPE: DNA
<213> ORGANISM: Artificial sequence
<220> FEATURE:
<223> OTHER INFORMATION: Probe sequence

<400> SEQUENCE: 6
atgcccatgt gttacatat                                         19

<210> SEQ ID NO 7
<211> LENGTH: 28
<212> TYPE: DNA
<213> ORGANISM: Artificial sequence
<220> FEATURE:
<223> OTHER INFORMATION: Amplification reaction primer

<400> SEQUENCE: 7
tctgatgcta atattctctg gctatttc                               28

<210> SEQ ID NO 8
<211> LENGTH: 21
<212> TYPE: DNA
<213> ORGANISM: Artificial sequence
<220> FEATURE:
<223> OTHER INFORMATION: Amplification reaction primer

<400> SEQUENCE: 8
tccagctgca acttcaggaa c                                      21

<210> SEQ ID NO 9
<211> LENGTH: 19
<212> TYPE: DNA
<213> ORGANISM: Artificial sequence
<220> FEATURE:
<223> OTHER INFORMATION: Probe sequence

<400> SEQUENCE: 9
catgattctc ggtgtttgt                                         19

<210> SEQ ID NO 10
<211> LENGTH: 19
<212> TYPE: DNA
<213> ORGANISM: Artificial sequence
<220> FEATURE:
<223> OTHER INFORMATION: Probe sequence
```

-continued

```
<400> SEQUENCE: 10
catgattctc agtgtttgt                                              19

<210> SEQ ID NO 11
<211> LENGTH: 22
<212> TYPE: DNA
<213> ORGANISM: Artificial sequence
<220> FEATURE:
<223> OTHER INFORMATION: Amplification reaction primer

<400> SEQUENCE: 11
tttgttttcc ttcaacggct tt                                          22

<210> SEQ ID NO 12
<211> LENGTH: 21
<212> TYPE: DNA
<213> ORGANISM: Artificial sequence
<220> FEATURE:
<223> OTHER INFORMATION: Amplification reaction primer

<400> SEQUENCE: 12
cgaccatttg ttcagttcgc t                                           21

<210> SEQ ID NO 13
<211> LENGTH: 15
<212> TYPE: DNA
<213> ORGANISM: Artificial sequence
<220> FEATURE:
<223> OTHER INFORMATION: Probe sequence

<400> SEQUENCE: 13
tcttggctga tttta                                                  15

<210> SEQ ID NO 14
<211> LENGTH: 15
<212> TYPE: DNA
<213> ORGANISM: Artificial sequence
<220> FEATURE:
<223> OTHER INFORMATION: Probe sequence

<400> SEQUENCE: 14
tcttggccga tttta                                                  15

<210> SEQ ID NO 15
<211> LENGTH: 22
<212> TYPE: DNA
<213> ORGANISM: Artificial sequence
<220> FEATURE:
<223> OTHER INFORMATION: Amplification reaction primer

<400> SEQUENCE: 15
tgcaaaattg ttccagaagc tg                                          22

<210> SEQ ID NO 16
<211> LENGTH: 21
<212> TYPE: DNA
<213> ORGANISM: Artificial sequence
<220> FEATURE:
<223> OTHER INFORMATION: Amplification reaction primer

<400> SEQUENCE: 16
tgtagaatgc cttggatccc a                                           21

<210> SEQ ID NO 17
```

```
<211> LENGTH: 17
<212> TYPE: DNA
<213> ORGANISM: Artificial sequence
<220> FEATURE:
<223> OTHER INFORMATION: Probe sequence

<400> SEQUENCE: 17
cagggaagtg gactgag                                                 17

<210> SEQ ID NO 18
<211> LENGTH: 16
<212> TYPE: DNA
<213> ORGANISM: Artificial sequence
<220> FEATURE:
<223> OTHER INFORMATION: Probe sequence

<400> SEQUENCE: 18
cagggaagcg gactga                                                  16

<210> SEQ ID NO 19
<211> LENGTH: 19
<212> TYPE: DNA
<213> ORGANISM: Artificial sequence
<220> FEATURE:
<223> OTHER INFORMATION: Amplification reaction primer

<400> SEQUENCE: 19
caagtcccct gtcggttcc                                               19

<210> SEQ ID NO 20
<211> LENGTH: 32
<212> TYPE: DNA
<213> ORGANISM: Artificial sequence
<220> FEATURE:
<223> OTHER INFORMATION: Amplification reaction primer

<400> SEQUENCE: 20
ctctagctgt aataagtaac aagcagtatc ct                                32

<210> SEQ ID NO 21
<211> LENGTH: 14
<212> TYPE: DNA
<213> ORGANISM: Artificial sequence
<220> FEATURE:
<223> OTHER INFORMATION: Probe sequence

<400> SEQUENCE: 21
cagcgcgttt gcat                                                    14

<210> SEQ ID NO 22
<211> LENGTH: 13
<212> TYPE: DNA
<213> ORGANISM: Artificial sequence
<220> FEATURE:
<223> OTHER INFORMATION: Probe sequence

<400> SEQUENCE: 22
cagcgccttt gca                                                     13

<210> SEQ ID NO 23
<211> LENGTH: 23
<212> TYPE: DNA
<213> ORGANISM: Artificial sequence
<220> FEATURE:
<223> OTHER INFORMATION: Amplification reaction primer

<400> SEQUENCE: 23
```

```
ttccattcta ggctacagct cca                                              23

<210> SEQ ID NO 24
<211> LENGTH: 18
<212> TYPE: DNA
<213> ORGANISM: Artificial sequence
<220> FEATURE:
<223> OTHER INFORMATION: Amplification reaction primer

<400> SEQUENCE: 24
caagacccgc tgagcctg                                                    18

<210> SEQ ID NO 25
<211> LENGTH: 20
<212> TYPE: DNA
<213> ORGANISM: Artificial sequence
<220> FEATURE:
<223> OTHER INFORMATION: Probe sequence

<400> SEQUENCE: 25
ctcagcaaat tccttgtcag                                                  20

<210> SEQ ID NO 26
<211> LENGTH: 20
<212> TYPE: DNA
<213> ORGANISM: Artificial sequence
<220> FEATURE:
<223> OTHER INFORMATION: Probe sequence

<400> SEQUENCE: 26
ctcagcaatt tccttgtcag                                                  20

<210> SEQ ID NO 27
<211> LENGTH: 26
<212> TYPE: DNA
<213> ORGANISM: Artificial sequence
<220> FEATURE:
<223> OTHER INFORMATION: Amplification reaction primer

<400> SEQUENCE: 27
ctgtgcaata accttcctag tacctg                                           26

<210> SEQ ID NO 28
<211> LENGTH: 31
<212> TYPE: DNA
<213> ORGANISM: Artificial sequence
<220> FEATURE:
<223> OTHER INFORMATION: Amplification reaction primer

<400> SEQUENCE: 28
atacttaaaa agaatcacat actcattcca a                                     31

<210> SEQ ID NO 29
<211> LENGTH: 13
<212> TYPE: DNA
<213> ORGANISM: Artificial sequence
<220> FEATURE:
<223> OTHER INFORMATION: Probe sequence

<400> SEQUENCE: 29
ttggccaagc ctg                                                         13

<210> SEQ ID NO 30
<211> LENGTH: 13
<212> TYPE: DNA
```

```
<213> ORGANISM: Artificial sequence
<220> FEATURE:
<223> OTHER INFORMATION: Probe sequence

<400> SEQUENCE: 30
ttggcgaagc ctg                                                     13

<210> SEQ ID NO 31
<211> LENGTH: 20
<212> TYPE: DNA
<213> ORGANISM: Artificial sequence
<220> FEATURE:
<223> OTHER INFORMATION: Amplification reaction primer

<400> SEQUENCE: 31
cccaagaacc atgctgcttt                                              20

<210> SEQ ID NO 32
<211> LENGTH: 18
<212> TYPE: DNA
<213> ORGANISM: Artificial sequence
<220> FEATURE:
<223> OTHER INFORMATION: Amplification reaction primer

<400> SEQUENCE: 32
gcccagggtg agggtagg                                                18

<210> SEQ ID NO 33
<211> LENGTH: 18
<212> TYPE: DNA
<213> ORGANISM: Artificial sequence
<220> FEATURE:
<223> OTHER INFORMATION: Probe sequence

<400> SEQUENCE: 33
agggaagatt ccactgca                                                18

<210> SEQ ID NO 34
<211> LENGTH: 17
<212> TYPE: DNA
<213> ORGANISM: Artificial sequence
<220> FEATURE:
<223> OTHER INFORMATION: Probe sequence

<400> SEQUENCE: 34
agggaaggtt ccactgc                                                 17
```

US 6,872,533 B2

STK15 (STK6) GENE POLYMORPHISM AND METHODS OF DETERMINING CANCER RISK

RELATED APPLICATION DATA

Application claims priority under 35 USC § 119(e) to U.S. Application Ser. Nos. 60/308,911 filed Jul. 27, 2001 and 60/334,146 filed Nov. 28, 2001. The disclosures of the prior applications are considered part of and are incorporated by reference in their entirety in the disclosure of this application.

GOVERNMENT SUPPORT

This invention was made in part with government support under Grants CA84244-03, CA84244-03 S1, and CA 89520-01 awarded by the National Cancer Institute. The government may have certain rights in this invention.

FIELD OF THE INVENTION

The present invention relates generally to determining the risk of developing cancer in an individual, and more specifically to methods and compositions for detecting a polymorphism in a specific gene, thereby providing a determination as to cancer risk.

BACKGROUND INFORMATION

Cancer is a disease of major impact in world health. In 1999, over 1 million people living in the United States alone, had been diagnosed with cancer. Furthermore, because of the aging of the population, this number is expected to double over the next fifty years. Therefore, there is a need to identify new agents for treating cancer. Furthermore, since effective treatment of cancer requires early and accurate diagnosis, there is a need for new methods for detecting and diagnosing cancer.

It is known that cancer is a genetic disorder. That is, an individual's particular genetic makeup influences whether and when the individual will develop cancer. Recent studies have focused on identifying the changes at a molecular level, that lead to cancer, in order to identify new diagnostics and treatment modalities. Studies of cancer predisposition have focused on genes in which mutations have a major impact on cancer formation and/or progression, called high penetrance genes. However, such genes although relatively easy to identify, account for only a small portion of cancer risk. The majority of cancer risk is associated with more difficult to find genes, known as low penetrance genes. Therefore, there is a need to identify low penetrance genes.

The human genome project has provided a tremendous amount of information regarding the nucleotide sequence of the human genome. However, this information was generated from analysis of the genomes of only a few individuals. Therefore, it does not provide sufficient information regarding the variability of the genome among individuals to allow an identification of differences between individuals that influence cancer risk. Therefore, there remains a need to identify differences between genomes of individuals which are responsible for the variability in cancer predisposition among individuals.

In addition to the characterization of human polymorphisms, identification of low penetrance tumor genes can be facilitated by identification of these genes in non-human species. Genomes of organisms, including mammals, are related, mainly because they arose from a common ancestor, and because basic cellular processes are conserved. Certain mammals, such as mice, lend themselves well to genetic studies in which the results of controlled animal crosses can be used to identify important regions of the genome for diseases such as cancer. However, there remains a need to develop methods which utilize genetics of non-human mammals to assist in the identification of regions of the human genome that are important for determining an individual's cancer disposition.

SUMMARY OF THE INVENTION

Identification of low penetrance tumor susceptibility genes has proven to be very difficult using standard methods. Experiments disclosed herein use linkage analysis and haplotype mapping followed by association studies using candidate genes at the orthologous human loci, to identify a polymorphism in the STK15/Aurora2 gene that is associated with increased human cancer risk (i.e. a STK15 susceptibility allele). For example, the polymorphism identified herein for the STK15 gene is associated with an increased risk of breast cancer. Furthermore, the susceptibility allele is preferentially amplified in human colon tumors. In the mouse, the STK6 allele inherited from the susceptible *musculus* parent is shown herein to be over-expressed in normal cells, and preferentially amplified in tumor cells from F1 hybrid mice. The approach described herein illustrates a method for identifying low penetrance cancer susceptibility genes by exploiting the advantages of combining mouse and human genetic strategies to identify cancer susceptibility genes.

In one aspect, the present invention provides a method for determining cancer susceptibility in a human subject, that includes identifying in a nucleic acid sample from the subject, a nucleotide occurrence of a single nucleotide polymorphism (SNP) of each copy of the STK15 gene corresponding to nucleotide 457 of SEQ ID NO:1. An occurrence of an adenosine residue at two or more copies of the SNP is associated with increased cancer susceptibility, thereby determining the cancer susceptibility of the human subject. The method can include determining whether the subject is homozygous for an adenosine residue at the SNP.

In another aspect, the present invention provides a method for determining cancer susceptibility in a human subject, wherein the method includes identifying in a nucleic acid sample from the subject, a nucleotide occurrence of a single nucleotide polymorphism (SNP) of the STK15 gene. The presence of the nucleotide occurrence is associated with cancer susceptibility, thereby providing a determination of the cancer susceptibility of the human subject. The SNP can correspond to nucleotide 457 of SEQ ID NO:1, and the nucleotide occurrence is thymidine or adenosine. In preferred embodiments, the nucleotide occurrence is an adenosine. In preferred embodiments, the method determining whether the nucleotide occurrences at nucleotide 457 of SEQ ID NO:1 are homozygous for adenosine. In certain embodiments, the human subject is of English or Finnish ancestry. The cancer can be any cancer, including colon cancer, breast cancer, or prostate cancer. In certain preferred embodiments, the cancer is breast cancer.

In another aspect, the present invention provides a method for detecting allele-specific amplification of an STK15 Ile31 allele of a human subject, that includes determining in a nucleic acid sample from the subject, the number of STK15 Ile31 alleles of the subject. Greater than two STK15 Ile31 alleles is indicative of the allele-specific amplification, thereby providing the detection of allele-specific amplification of the STK15 Ile31 allele. The sample can include an isolated cell of the mammalian subject. The isolated cell can be from a biopsy, for example a biopsy of breast tissue, prostate tissue, and/or colon tissue. In certain preferred embodiments, the tissue is breast tissue.

In another aspect, the present invention provides a method for identifying a test agent which affects STK15 activity, that includes contacting an isolated human cell with the test agent, and analyzing STK15 activity in the isolated cell. The isolated human cell includes one or more copies of an STK15 gene that includes an adenosine residue at a position corresponding to nucleotide 457 of SEQ ID NO:1.

In certain preferred embodiments of this aspect of the invention, the isolated human cell comprises two or more copies of the STK15 gene, that include an adenosine residue at a position corresponding to nucleotide 457 of SEQ ID NO:1. The STK15 analyzed can be STK15 kinase activity. In certain embodiments, the test agent is a small organic compound or an antibody. The isolated human cell that is utilized in the method can include an adenosine residue at a position on each copy of chromosome 20 or amplification product thereof, corresponding to nucleotide 457 of SEQ ID NO:1. By identifying a test agent that affects STK15 activity, the method further identifies a test agent that affects cell proliferation.

In another aspect, the present invention provides a method for identifying a low penetrance cancer susceptibility gene, that includes identifying in a nucleic acid sample of a subject, allele-specific amplification of an endogenous polynucleotide suspected of being associated with cancer. Amplification of the allele indicates that the allele is of a low penetrance cancer-susceptibility gene, thereby providing the detection of the low penetrance cancer susceptibility gene. The nucleic acid sample can be from a tumor. The nucleic acid sample can be from a colon, breast, or prostate tumor, in certain preferred embodiments a breast tumor.

In another aspect, the present invention provides a method for identifying a human low penetrance cancer susceptibility allele, that includes:

a) identifying one or more general genetic loci involved in tumor susceptibility by crossing a first organism of a first strain of a first non-human mammalian species of a first genus with a second organism of either a second strain of the first non-human mammalian species or a first strain of a second non-human mammalian species of the first genus, the second organism having a different tumor susceptibility than the first organism, and comparing the genomes of progeny with different tumor susceptibility;

b) identifying a more finely mapped genetic locus involved in tumor susceptibility by analyzing a cancer correlation of haplotypes of the general genetic loci, the more finely mapped genetic locus being found within the one or more general genetic loci;

c) identifying a candidate human gene on a target human genome locus that is orthologous to the more finely mapped locus, and d) identifying alleles in the candidate human gene that exhibit different genotype frequencies between normal healthy controls and subjects having cancer, thereby identifying a human low penetrance cancer susceptibility allele.

In another aspect the present invention provides a method for identifying a human low penetrance cancer susceptibility allele, wherein the method includes:

a) identifying one or more general genetic loci involved in tumor susceptibility by crossing a first inbred organism of a first mouse strain or first mouse species with a first outbred organism of either a second mouse strain or a second mouse species, the first outbred organism having a different tumor susceptibility than the first inbred organism, and comparing the genomes of progeny with different tumor susceptibility;

b) identifying a more finely mapped genetic locus involved in tumor susceptibility by analyzing a cancer correlation of haplotypes of the general genetic loci, the more finely mapped genetic locus being found within the one or more general genetic loci;

c) identifying a candidate human gene on a target human genome locus that is orthologous to the more finely mapped locus, and d) identifying alleles in the candidate human gene that exhibit different genotype frequencies between normal healthy controls and subjects having cancer, thereby identifying a human low penetrance cancer susceptibility allele. Step b can further include linkage analysis. In preferred embodiments, the first outbred organisms can be *Mus spretus* and the first inbred organism can be a *Mus musculus*. Step a can further include backcrossing.

In another aspect, the present invention provides a method for determining cancer susceptibility of a human subject, that includes determining in a nucleic acid sample from the subject, the number of STK15 Ile31 alleles of the subject. In this aspect, greater than two TK6 Ile31 alleles is indicative of an increased susceptibility to cancer, thereby determining cancer susceptibility. The sample can include an isolated cell from the subject, such as a cell from a biopsy. The biopsy, in certain embodiments, is from breast, colon, or prostate tissue. In certain preferred embodiments, the biopsy is from breast tissue.

STK6 allele, most likely causing the observed over expression. Asterisks indicate significant differences between genomic DNA and cDNA samples. The means and standard deviations of three independent experiments are shown. For panel b, cDNA was prepared from other skin tumor-derived *musculus/spretus* hybrid cell lines. Six of these, derived from independent tumors, showed significant over expression of the *musculus* allele indicated by asterisks. For panel c, genomic DNA was isolated from the same samples shown in b, and TaqMan® analysis was carried out to measure gene copy number of STK6. Four of the samples (denoted by asterisks) showed significant amplification of the *musculus* allele of STK6.

Figure 4:
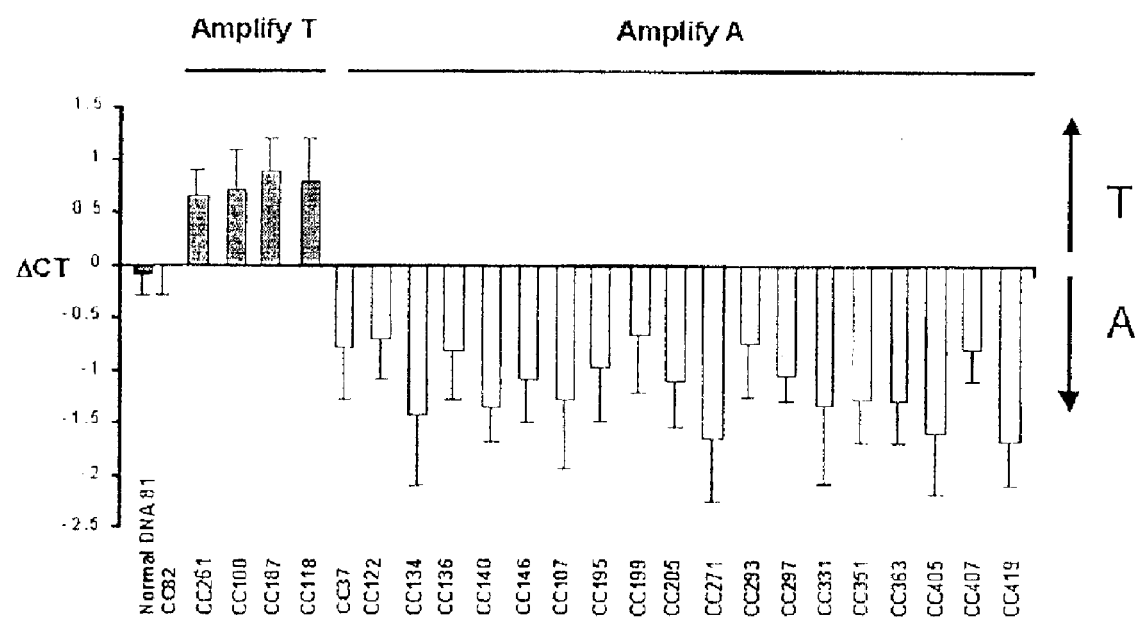

FIG. 4 is a graph of colon tumor amplification of STK15 alleles. DNA was prepared from paired normal colon mucosa and colon adenocarcinomas. Normal DNAs were genotyped for the AA31 SNP. The ratio between the Phe31 and Ile31 alleles in heterozygous colon tumors was determined by TaqMan® analysis using allele specific probes and is expressed as differences in CT levels (cycles) with positive DCT values indicating amplification of the Phe (T) allele and negative DCT values of the Ile (A) allele. Of 48 samples typed, 4 showed amplification of the Phe allele greater than 0.6 CTs (samples in gray) and 19 showed amplification of the Ile allele (samples in white). 21 samples showed no difference between normal and tumor DNA (one pair shown in black). Four samples showed amplification differences of less than 0.6 CTs and were scored as uncertain (not shown). The normalized means and standard deviations of three independent experiments are shown.

Figure 5:
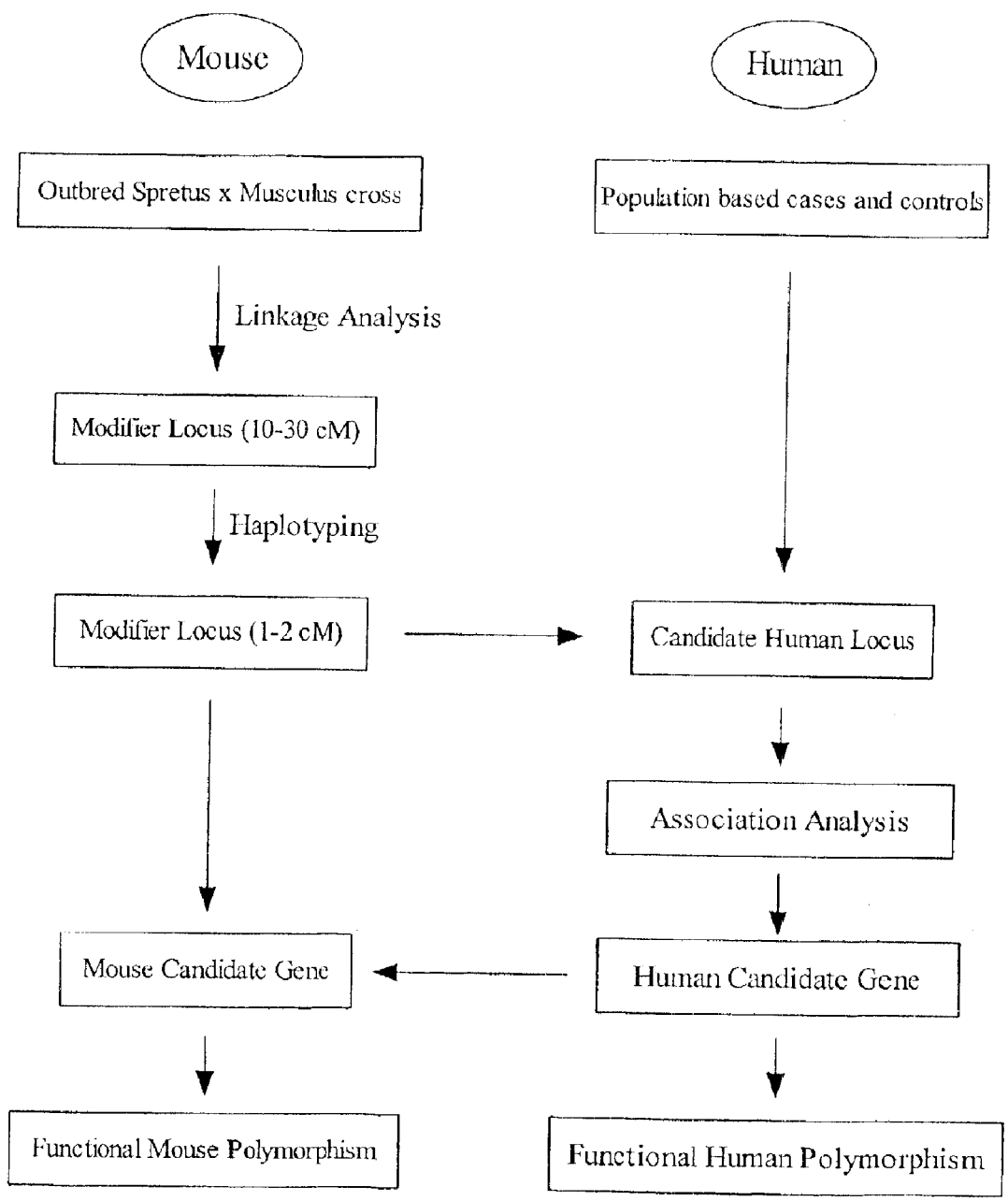

FIG. 5 is a diagram of a preferred embodiment of the combined mouse-human method of the present invention, for identifying low penetrance tumor susceptibility genes.

DETAILED DESCRIPTION OF THE INVENTION

The present invention provides a method for determining cancer susceptibility in a human subject. The methods include identifying in a nucleic acid sample from the subject, a nucleotide occurrence of a single nucleotide polymorphism (SNP) of the STK15 gene. The presence of the nucleotide occurrence is associated with cancer susceptibility, thus providing a determination of the cancer susceptibility of the human subject. In one preferred embodiment, the SNP corresponds to nucleotide 457 of SEQ ID NO:1.

A polymorphism, referred to herein as STK15 F31I (nucleotide 457 of SEQ ID NO:1), is identified herein, in the STK15 gene, in which Ile homozygotes have an increased risk for developing cancer, for example breast cancer. The polymorphism is the result of a SNP at nucleotide 457 of SEQ ID NO:1 (position 457 of Genbank XM_114165; position 347 of NM_003600; and dbSNP 3171189). This SNP involves a nucleotide occurrence of an adenosine or a thymidine at this nucleotide position. An adenosine at this SNP encodes an Isoleucine residue at amino acid position 31 of the STK15 protein, whereas a thymidine occurrence at this SNP encodes a phenylalanine reside at amino acid position 31. Therefore, polymorphisms in which an adenosine occurs at this SNP are referred to herein as STK15 Ile31. As shown in Table 2, the predominant genotype (i.e. the major genotype) of at least some human populations is a TT homozygous genotype. However, a homozygous AA genotype at this SNP is associated with cancer risk, such as breast cancer risk.

Accordingly, the nucleotide occurrence determined by methods of the present invention for nucleotide 457 of SEQ ID NO:1 can be an adenosine. The methods of the present invention, in preferred embodiments, identify whether a subject is heterozygous or homozygous at a position corresponding to nucleotide 457 of SEQ ID NO:1. Preferably, the methods of the present invention identifies whether an individual is homozygous for the STK15 Ile31 allele. That is, the method identifies whether a diploid pair of nucleotide occurrences at a position corresponding to nucleotide 457 of SEQ ID NO:1 (the STK15 F31I SNP) (or nucleotide 9 of SEQ ID NO:25 and SEQ ID NO:26), are adenosine residues.

A method according to the present invention can identify a nucleotide occurrence for either strand of DNA, typically genomic DNA. Accordingly, it will be recognized that for embodiments in which a nucleotide occurrence at a position corresponding to nucleotide 457 of SEQ ID NO:1 (the STK15 F31I SNP) is identified, the method can identify a nucleotide in the opposite strand to that listed in SEQ ID NO:1. For these embodiments, the method determines cancer risk based on a complementary nucleotide. For example, where the opposite strand to that corresponding to SEQ ID NO:1 is analyzed, a homozygous thymidine occurrence at a nucleotide corresponding to nucleotide 457 of SEQ ID NO:1 in an opposite or complementary strand, will provide an identification of a homozygous STK15 Ile31 allele, and an increased susceptibility to cancer.

The results presented herein identify STK15 Ile31 as a low penetrance susceptibility allele. As indicated above, the sequence listing provides the nucleotide flanking sequences for the STK15 F31I SNP of the present invention. It will be recognized that the 5' and 3' flanking sequences exemplified herein, provide sufficient information to identify the SNP location within the human STK15 gene.

Serine/threonine kinase 15 (STK15) (Genbank NM_003600; Genbank NP_00351; Genbank XM_114165), is a member of the Aurora/Ip11p family of mitotically regulated serine/threonine kinases that are key regulators of chromosome segregation and cytokinesis (Bischoff, J. R. & Plowman, G. D., *Trends Cell Biol.* 9, 454–459 (1999)). The human version of this gene has also been referred to as STK6 (See e.g. Genbank NM_003158; Kimura et al., *J. Biol. Chem.* 272, 1376 (1997)). The mouse homolog of the human STK15 gene is referred to as serine/threonine kinase 6 (STK6). STK15 (STK6) encodes a centrosome-associated kinase that is highly expressed at the G2 and M phase of the cell cycle (Bischoff & Plowman (1999)). A variety of primary human tumor types including 52% of colorectal, 38% of ovarian, and 12% of breast tumors show amplification of STK15. Functional data exists showing that overexpression of the normal STK15 allele leads to centrosome amplification, chromosomal instability and transformation (Tanner, M. M. et al., *Clin. Cancer Res.* 6, 1833–1839 (2000); Zhou, H. et al., *Nature Genet.* 20, 189–193 (1998); Bischoff, J. R. et al., *EMBO J.* 17, 3052–3065 (1998); Sen, S., et al., *Oncogene* 14, 2195–2200 (1997); Miyoshi, Y., et al., *Int. J. Cancer* 92, 370–373 (2001)). Immunohistochemical analyses revealed overexpression of STK15 in 94% of invasive ductal adenocarcinomas of the breast, which is intriguing since genetic instability is an early event in the development of ductal breast carcinoma (Tanaka, T. et al., *Cancer Res.* 59, 2041–2044 (1999); and Romanov, S. R. et al., *Nature* 409, 633–637 (2001)).

It will be understood that a method of the present invention can be used to determine an increase or decrease in cancer susceptibility or risk for a subject, depending on the particular SNP (i.e., polymorphism). As such, the term "Associated with cancer susceptibility" can refer to an occurrence of a particular polymorphism as placing a subject at an increased risk of cancer, or a decreased risk of cancer. For example, as indicated above, the STK15 Ile31 polymorphism, is associated with an increased cancer risk. The association between an STK15 polymorphism and cancer is typically identified, using a statistical analysis of population data. As will be recognized many known statistical methods can be used for this analysis. Typically, an association is identified when a statistical analysis result shows an association between a STK15 polymorphism and cancer susceptibility, with at least 80%, 85%, 90%, 95%, or 99%, most preferably 95% confidence. The statistical tools may test for significance related to a null hypothesis that an on-test polymorphic allele is not significantly different between the groups.

As used herein, the terms "determine," "determining," "infer" or "inferring", when used in reference to cancer susceptibility, means drawing a conclusion about susceptibility to cancer using a process of analyzing the nucleotide sequence of a polynucleotide comprising a polymorphic site of the present invention, such as the STK6F31I SNP, in a nucleic acid sample of the subject, and comparing the individual or combination of nucleotide occurrence(s) of the SNP(s) to known relationships of nucleotide occurrence(s) of the STK15 SNP(s) to cancer risk (i.e. cancer susceptibility). For example, an identification of homozygous adenosine alleles at a position corresponding to nucleotide 457 of SEQ ID NO:1 (the STK15 F31I SNP), leads to a determination that a subject is at an increased risk for developing cancer. As disclosed herein, the nucleotide occurrence(s) can be identified directly by examining nucleic acid molecules, or indirectly by examining a polypeptide encoded by polymorphic gene, wherein the polymorphism is associated with an amino acid change in the encoded polypeptide. Quantitative determinations of cancer susceptibility (i.e. cancer risk) can be made using statistical analysis of results similar to those disclosed in Table 2.

The methods of the present invention that determine cancer susceptibility also can be used to assist to in characterizing a cancer of a subject, or in prognosing, detecting, and/or diagnosing cancer. The sample can be, for example, taken from a suspicious lesion or tumor, as described in further detail herein. Thus, determining whether a subject is homozygous for the STK15 Ile 31, for example can be used to assist in determining a treatment, since this homozygosity can indicate an increased perpensity for chromosomal instability.

Polymorphisms are allelic variants that occur in a population. As such, a single nucleotide polymorphism (SNP) is characterized by the presence in a population of one or two, three or four nucleotides (i.e., adenosine, cytosine, guanosine or thymidine), typically less than all four nucleotides, at a particular locus in a genome such as the human genome. It will be recognized that, while the methods of the invention are exemplified by the detection of one SNP, the STK15 F31I SNP, the methods can be used to identify other STK15 SNPs either alone or in combination with STK15 F31I, or combined with methods for determining other STK15 polymorphisms, or polymorphisms in other cancer susceptibility genes, to increase the accuracy of the determination (i.e. the power of the inference).

The present invention relates to methods for determining cancer susceptibility in a human subject. The methods can be used to determine susceptibility to a variety of cancers or other types of cell proliferative disorders. In preferred embodiments, the methods of the present invention determine breast, prostate, or colon cancer susceptibility. For preferred embodiments that involve identifying a nucleotide occurrence at a position corresponding to nucleotide 457 of SEQ ID NO:1 (STK15 F3 1I), breast cancer susceptibility is determined.

A "cell proliferative disorder" or "cellular proliferative disorder" is any disorder in which the proliferative capabilities of the affected cells is different from the normal proliferative capabilities of unaffected cells. An example of a cell proliferative disorder is cancer. The present invention can be used to identify SNPs related to any type of cancer, of which many are known. Cancers include, for non-limiting example, malignant astrocytoma, glioblastoma, and medulloblastoma, gastric cancer, colorectal cancer, colorectal adenoma, acute myelogenous leukemia, lung cancer, renal cancer, leukemia, breast cancer, prostate cancer, endometrial cancer and neuroblastoma.

A cell proliferative disorder as described herein can be any neoplasm. Such neoplasms are either benign or malignant. The term "neoplasm" refers to a new, abnormal growth of cells or a growth of abnormal cells that reproduce faster than normal. A neoplasm creates an unstructured mass (a tumor) which can be either benign or malignant. For example, the neoplasm may be a head, neck, lung, esophageal, stomach, prostate, small bowel, colon, bladder, kidney, or cervical neoplasm. The term "benign" refers to a tumor that is noncancerous, e.g. its cells do not proliferate or invade surrounding tissues. The term "malignant" refers to a tumor that is metastatic or no longer under normal cellular growth control.

As used herein, the term "at least one", when used in reference to a gene, SNP, or the like, means 1, 2, 3, 4, 5, 6, 7, 8, 9, 10, etc. Reference to "at least a second" gene, SNP, or the like, for example, means two or more, i.e., 2, 3, 4, 5, 6, 7, 8, 9, 10, etc., genes.

The attached sequence listing provides flanking nucleotide sequences (SEQ ID NO:1) for the STK15 F31I SNP disclosed herein. These flanking sequence serve to aid in the identification of the precise location of the SNPs in the human genome, and serve as target gene segments useful for performing methods of the invention. A target polynucleotide typically includes a SNP locus and a segment of a corresponding gene that flanks the SNP. Primers and probes that selectively hybridize at or near the target polynucleotide sequence, as well as specific binding pair members that can specifically bind at or near the target polynucleotide sequence, can be designed based on the disclosed gene sequences and information provided herein.

The subject for the methods of the present invention can be a subject of any race or national origin. In certain embodiments where the methods include identifying a nucleotide occurrence corresponding to nucleotide 457 of SEQ ID NO:1, the subject is of Finnish and English ancestry. In certain preferred examples of these embodiments, the cancer is breast cancer.

As used herein, the term "selective hybridization" or "selectively hybridize," refers to hybridization under moderately stringent or highly stringent conditions such that a nucleotide sequence preferentially associates with a selected nucleotide sequence over unrelated nucleotide sequences to a large enough extent to be useful in identifying a nucleotide occurrence of a SNP. In certain preferred embodiments, as discussed herein, the SNP corresponds to nucleotide 457 of SEQ ID NO:1 (the STK15 F31I SNP). It will be recognized that some amount of non-specific hybridization is unavoidable, but is acceptable provide that hybridization to a target nucleotide sequence is sufficiently selective such that it can be distinguished over the non-specific cross-hybridization, for example, at least about 2-fold more selective, generally at least about 3-fold more selective, usually at least about 5-fold more selective, and particularly at least about 10-fold more selective, as determined, for example, by an amount of labeled oligonucleotide that binds to target nucleic acid molecule as compared to a nucleic acid molecule other than the target molecule, particularly a substantially similar (i.e., homologous) nucleic acid molecule other than the target nucleic acid molecule. Conditions that allow for selective hybridization can be determined empirically, or can be estimated based, for example, on the relative GC:AT content of the hybridizing oligonucleotide and the sequence to which it is to hybridize, the length of the hybridizing oligonucleotide, and the number, if any, of mismatches between the oligonucleotide and sequence to which it is to hybridize (see, for example, Sambrook et al., "Molecular Cloning: A laboratory manual (Cold Spring Harbor Laboratory Press 1989)).

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

The term "polynucleotide" is used broadly herein to mean a sequence of deoxyribonucleotides or ribonucleotides that are linked together by a phosphodiester bond. For convenience, the term "oligonucleotide" is used herein to refer to a polynucleotide that is used as a primer or a probe. Generally, an oligonucleotide useful as a probe or primer that selectively hybridizes to a selected nucleotide sequence is at least about 15 nucleotides in length, usually at least about 18 nucleotides, and particularly about 21 nucleotides or more in length.

A polynucleotide can be RNA or can be DNA, which can be a gene or a portion thereof, a cDNA, a synthetic polydeoxyribonucleic acid sequence, or the like, and can be single stranded or double stranded, as well as a DNA/RNA hybrid. In various embodiments, a polynucleotide, including an oligonucleotide (e.g., a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide or oligonucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., Nucl. Acids Res. 22:5220–5234 (1994); Jellinek et al., Biochemistry 34:11363–11372 (1995); Pagratis et al., Nature Biotechnol. 15:68–73 (1997), each of which is incorporated herein by reference).

The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., Nucl. Acids Res. 22:977–986 (1994); Ecker and Crooke, BioTechnology 13:351360 (1995), each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide or oligonucleotide comprising nucleotide analogs or covalent bonds other than phosphodiester bonds generally are chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995). Thus, the term polynucleotide as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR).

In various embodiments, it can be useful to detectably label a polynucleotide or oligonucleotide. Detectable labeling of a polynucleotide or oligonucleotide is well known in the art. Particular non-limiting examples of detectable labels include chemiluminescent labels, radiolabels, enzymes, haptens, or even unique oligonucleotide sequences.

A method of the identifying a SNP of the STK15 gene, including a SNP corresponding to nucleotide 457 of SEQ ID NO:1, also can be performed using a specific binding pair member. As used herein, the term "specific binding pair member" refers to a molecule that specifically binds or selectively hybridizes to another member of a specific binding pair. Specific binding pair member include, for example, probes, primers, polynucleotides, antibodies, etc. For example, a specific binding pair member includes a primer or a probe that selectively hybridizes to a target polynucleotide that includes a SNP loci, or that hybridizes to an amplification product generated using the target polynucleotide as a template.

As used herein, the term "specific interaction," or "specifically binds" or the like means that two molecules form a complex that is relatively stable under physiologic conditions. The term is used herein in reference to various interactions, including, for example, the interaction of an antibody that binds a polynucleotide that includes a SNP site; or the interaction of an antibody that binds a polypeptide that includes an amino acid that is encoded by a codon that includes a SNP site. According to methods of the invention, an antibody can selectively bind to a polypeptide that includes a particular amino acid encoded by a codon that includes a SNP site. Alternatively, an antibody may preferentially bind a particular modified nucleotide that is incorporated into a SNP site for only certain nucleotide occurrences at the SNP site, for example using a primer extension assay.

A specific interaction can be characterized by a dissociation constant of at least about $1\times10^{-6}$ M, generally at least about $1\times10^{-7}$ M, usually at least about $1\times10^{-8}$ M, and particularly at least about $1\times10^{-9}$ M or $1\times10^{-10}$ M or greater. A specific interaction generally is stable under physiological conditions, including, for example, conditions that occur in a living individual such as a human or other vertebrate or invertebrate, as well as conditions that occur in a cell culture such as used for maintaining mammalian cells or cells from another vertebrate organism or an invertebrate organism. Methods for determining whether two molecules interact specifically are well known and include, for example, equilibrium dialysis, surface plasmon resonance, and the like.

The present invention in another aspect provides a method for detecting a nucleotide occurrence at a position corresponding to nucleotide 457 of SEQ ID NO:1. The method includes incubating a sample comprising a polynucleotide with a specific binding pair member, wherein the specific binding pair member specifically binds at or near an adenosine residue at a position corresponding to nucleotide 457 of SEQ ID NO:1. The method further includes detecting selective binding of the specific binding pair member, wherein selective binding is indicative of the presence of the adenosine residue at the position corresponding to nucleotide 457 of SEQ ID NO:1. According to the present invention, selective binding can be identified using an amplification reaction, a primer extension reaction, or any other known method for detecting selective binding of a nucleotide, as described below.

In another aspect, the present invention provides a method for detecting a nucleotide occurrence at a position corresponding to a SNP of Table 3, particularly the SNPs of Table 3 that were not previously reported (See Table 3). Preferably, the nucleotide occurrence of the SNP of Table 3 identified by the method is the minor (i.e. less frequent) nucleotide occurrence.

Numerous methods are known in the art for determining the nucleotide occurrence for a particular SNP in a sample. Such methods can utilize one or more oligonucleotide probes or primers, including, for example, an amplification primer pair, that selectively hybridize to a target polynucleotide, which contains one or more SNPs, such as the nucleotide 457 of SEQ ID NO:1. Oligonucleotide probes useful in practicing a method of the invention can include, for example, an oligonucleotide that is complementary to and spans a portion of the target polynucleotide, including the position of the SNP, wherein the presence of a specific nucleotide at the position (i.e., the SNP) is detected by the presence or absence of selective hybridization of the probe. Such a method can further include contacting the target polynucleotide and hybridized oligonucleotide with an endonuclease, and detecting the presence or absence of a cleavage product of the probe, depending on whether the nucleotide occurrence at the SNP site is complementary to the corresponding nucleotide of the probe.

An oligonucleotide ligation assay also can be used to identify a nucleotide occurrence at a polymorphic position, wherein a pair of probes that selectively hybridize upstream and adjacent to and downstream and adjacent to the site of the SNP, and wherein one of the probes includes a terminal nucleotide complementary to a nucleotide occurrence of the SNP. Where the terminal nucleotide of the probe is complementary to the nucleotide occurrence, selective hybridization includes the terminal nucleotide such that, in the presence of a ligase, the upstream and downstream oligonucleotides are ligated. As such, the presence or absence of a ligation product is indicative of the nucleotide occurrence at the SNP site.

An oligonucleotide also can be useful as a primer, for example, for a primer extension reaction, wherein the product (or absence of a product) of the extension reaction is indicative of the nucleotide occurrence. In addition, a primer pair useful for amplifying a portion of the target polynucleotide including the SNP site can be useful, wherein the amplification product is examined to determine the nucleotide occurrence at the SNP site. Particularly useful methods include those that are readily adaptable to a high throughput format, to a multiplex format, or to both. The primer extension or amplification product can be detected directly or indirectly and/or can be sequenced using various methods known in the art. Amplification products which span a SNP loci can be sequenced using traditional sequence methodologies (e.g., the "dideoxy-mediated chain termination method," also known as the "Sanger Method" (Sanger, F., et al., *J. Molec. Biol.* 94:441 (1975); Prober et al. *Science* 238:336–340 (1987)) and the "chemical degradation method," "also known as the "Maxam-Gilbert method" (Maxam, A. M., et al., *Proc. Natl. Acad. Sci.* (U.S.A.) 74:560 (1977)), both references herein incorporated by reference) to determine the nucleotide occurrence at the SNP loci.

Methods of the invention can identify nucleotide occurrences at SNPs using a "microsequencing" method. Microsequencing methods determine the identity of only a single nucleotide at a "predetermined" site. Such methods have particular utility in determining the presence and identity of polymorphisms in a target polynucleotide. Such microsequencing methods, as well as other methods for determining the nucleotide occurrence at a SNP loci are discussed in Boyce-Jacino, et al., U.S. Pat. No. 6,294,336, incorporated herein by reference, and summarized herein.

Microsequencing methods include the Genetic Bit Analysis™ method disclosed by Goelet, P. et al. (WO 92/15712, herein incorporated by reference). Additional, primer-guided, nucleotide incorporation procedures for assaying polymorphic sites in DNA have also been described (Komher, J. S. et al, *Nucl. Acids. Res.* 17:7779–7784 (1989); Sokolov, B. P., *Nucl. Acids Res.* 18:3671 (1990); Syvanen, A. -C., et al., *Genomics* 8:684–692 (1990); Kuppuswamy, M. N. et al., *Proc. Natl. Acad. Sci.* (*U.S.A.*) 88:1143–1147 (1991); Prezant, T. R. et al, *Hum. Mutat.* 1:159–164 (1992); Ugozzoli, L. et al., GATA 9:107–112 (1992); Nyren, P. et al., *Anal. Biochem.* 208:171–175 (1993); and Wallace, WO89/10414). These methods differ from Genetic Bit™ analysis in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A. -C., et al. *Amer. J. Hum. Genet.* 52:46–59 (1993)).

Alternative microsequencing methods have been provided by Mundy, C. R. (U.S. Pat. No. 4,656,127) and Cohen, D. et al (French Patent 2,650,840; PCT Appln. No. WO91/02087) which discusses a solution-based method for determining the identity of the nucleotide of a polymorphic site. As in the Mundy method of U.S. Pat. No. 4,656,127, a primer is employed that is complementary to allelic sequences immediately 3'-to a polymorphic site.

In response to the difficulties encountered in employing gel electrophoresis to analyze sequences, alternative methods for microsequencing have been developed. Macevicz (U.S. Pat. No. 5,002,867), for example, describes a method for determining nucleic acid sequence via hybridization with multiple mixtures of oligonucleotide probes. In accordance with such method, the sequence of a target polynucleotide is determined by permitting the target to sequentially hybridize with sets of probes having an invariant nucleotide at one position, and a variant nucleotides at other positions. The Macevicz method determines the nucleotide sequence of the target by hybridizing the target with a set of probes, and then determining the number of sites that at least one member of the set is capable of hybridizing to the target (i.e., the number of "matches"). This procedure is repeated until each member of a sets of probes has been tested.

Boyce-Jacino, et al., U.S. Pat. No. 6,294,336 provides a solid phase sequencing method for determining the sequence of nucleic acid molecules (either DNA or RNA) by utilizing a primer that selectively binds a polynucleotide target at a site wherein the SNP is the most 3' nucleotide selectively bound to the target.

In one particular commercial example of a method that can be used to identify a nucleotide occurrence of one or more SNPs, the nucleotide occurrences of an STK15 SNP, in preferred embodiments an STK15 SNP corresponding to nucleotide 457 of SEQ ID NO:1, in a sample can be determined using the SNP-IT™ method (Orchid BioSciences, Inc., Princeton, N.J.). In general, SNP-IT™ is a 3-step primer extension reaction. In the first step a target polynucleotide is isolated from a sample by hybridization to a capture primer, which provides a first level of specificity. In a second step the capture primer is extended from a terminating nucleotide trisphosphate at the target SNP site, which provides a second level of specificity. In a third step, the extended nucleotide trisphosphate can be detected using a variety of known formats, including: direct fluorescence, indirect fluorescence, an indirect colorimetric assay, mass spectrometry, fluorescence polarization, etc. Reactions can be processed in 384 well format in an automated format using a SNPstream™ instrument (Orchid BioSciences, Inc., Princeton, N.J.).

In another embodiment, a method of the present invention can be performed by amplifying a polynucleotide region that includes an STK15 SNP, capturing the amplified product in an allele specific manner in individual wells of a microtiter plate, and detecting the captured target allele.

In a specific non-limiting example of a method for identifying a nucleotide occurrence at the STK15 F31I SNP, a primer pair is synthesized that comprises a forward primer that hybridizes to a sequence 5' to the SNP of SEQ ID NO:1 (the SEQ ID corresponding to this marker and a reverse primer that hybridizes to the opposite strand of a sequence 3' to the SNP of SEQ ID NO:1. This primer pair is used to amplify a target polynucleotide that includes the STK15 F31I SNP, to generate an amplification product. A third primer can then be used as a substrate for a primer extension reaction. The third primer can bind to the amplification product such that the 3' nucleotide of the third primer (e.g., adenosine) binds to the STK15 F31I SNP site and is used for a primer extension reaction. The primer can be designed and conditions determined such that the primer extension reaction proceeds only if the 3' nucleotide of the third primer is complementary to the nucleotide occurrence at the SNP. For example, the third primer can be designed such that the primer extension reaction will proceed if the nucleotide occurrence for marker STK15 F31I is an adenosine, for example, but not if the nucleotide occurrence of the marker is a thymidine.

Accordingly, using the methods described above, the nucleotide occurrence of a SNP, for example the STK15 F31I SNP, can be identified using for example, an amplification reaction, a primer extension reaction, or an immu-noassay. The nucleotide occurrence of the SNP can also be identified by contacting polynucleotides in the sample or polynucleotides derived from the sample, with a specific binding pair member that selectively hybridizes to a polynucleotide region comprising the a nucleotide occurrence of a SNP, under conditions wherein the binding pair member specifically binds at or near the SNP. The specific binding pair member can be an antibody or a polynucleotide.

Antibodies that are used in the methods of the invention include antibodies that specifically bind polynucleotides that encompass an STK15 SNP, in preferred embodiments the STK6F31I SNP. In addition, antibodies of the invention bind polypeptides that include an amino acid encoded by a codon that includes an STK15 SNP. For example, the antibody can specifically bind to an STK15 polypeptide including an isoleucine, but not a phenylalanine residue, at a position corresponding to amino acid 31 of the human STK15 gene product.

Antibodies are well-known in the art and discussed, for example, in U.S. Pat. No. 6,391,589. Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Antibodies of the invention include antibody fragments that include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. The antibodies of the invention may be monospecific, bispecific, trispecific or of greater multispecificity.

The antibodies of the invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette- Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example; in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

As indicated above, where the particular nucleotide occurrence of a SNP is such that the nucleotide occurrence results in an amino acid change in an encoded polypeptide, as is the case for the STK15 F31I SNP, the nucleotide occurrence can be identified indirectly by detecting the particular amino acid in the polypeptide. The method for determining the amino acid will depend, for example, on the structure of the polypeptide or on the position of the amino acid in the polypeptide.

Where the polypeptide contains only a single occurrence of an amino acid encoded by the particular SNP, the polypeptide can be examined for the presence or absence of the amino acid. For example, where the amino acid is at or near the amino terminus or the carboxy terminus of the polypeptide, simple sequencing of the terminal amino acids can be performed. Alternatively, the polypeptide can be treated with one or more enzymes and a peptide fragment containing the amino acid position of interest can be examined, for example, by sequencing the peptide, or by detecting a particular migration of the peptide following electrophoresis. Where the particular amino acid comprises an epitope of the polypeptide, the specific binding, or absence thereof, of an antibody specific for the epitope can be detected. Other methods for detecting a particular amino acid in a polypeptide or peptide fragment thereof are well known and can be selected based, for example, on convenience or availability of equipment such as a mass spectrometer, capillary electrophoresis system, magnetic resonance imaging equipment, and the like.

In another aspect, the present invention provides a method for detecting allele-specific amplification of an STK15 Ile31 allele of a human subject. The method includes determining in a nucleic acid sample from the subject, the number of STK15 Ile31 alleles of the subject, wherein greater than two STK15 Ile31 alleles is indicative of the allele-specific amplification. The sample for this aspect of the invention typically includes an isolated cell of the mammalian subject. The isolated cell can be from a biopsy, for example a breast or colon biopsy. In certain preferred embodiments, the sample is from a colon biopsy. "Selectively amplification" or "allele-specific amplification" means that only certain polymorphic versions of a gene, or portion thereof, are amplified.

Methods of the present invention directed at detecting allele-specific amplification of an STK15 Ile31 allele have numerous utilities. For example, such methods can be used to determine whether a subject has an increased susceptibility to developing cancer. As such, another aspect of the present invention is a method for determining cancer susceptibility of a human subject, by determining in a nucleic acid sample from the subject, the number of STK15 Ile31 alleles of the subject. Greater than two TK6 Ile31 alleles is indicative of an increased susceptibility to cancer.

The results illustrated herein in the Examples section, identify the STK15 Ile31 allele, as an allele that is selectively amplified. Combined with known characteristics concerning STK15 (STK6) discussed above, the allele-specific amplification of STK15 (STK6) presented herein, identifies this gene as a low-penetrance tumor susceptibility gene.

This result illustrates another aspect of the present invention which provides a method for identifying a low penetrance cancer susceptibility gene, by identifying in a nucleic acid sample of a subject, allele-specific amplification of an endogenous polynucleotide. The amplification of the allele suggests that the allele is of a low penetrance cancer-susceptibility gene. In certain preferred embodiments of this aspect of the invention, the nucleic acid sample is from a biopsy, such as a tumor biopsy, or another lesion in which a characterization of the lesion is important for diagnosis, prognosis, or treatment. For example, a skin lesion suspected of being cancer. As another example, the sample can be from a colon tumor or a breast tumor, wherein STK15 amplification is known (Zhou, H. et al., supra (1998); and Bischoff, J. R. et al., supra (1998)). Since STK15 is amplified in approximately 50% of colon tumors, in preferred embodiments of this aspect of the invention, the sample is from a colon tumor. (Zhou, H. et al., supra (1998); and Bischoff, J. R. et al., supra (1998)).

Typically, the endogenous polynucleotide according to this aspect of the invention, is suspected of being associated with cancer. The polynucleotide can be suspected of being associated with cancer because it has at least one characteristic, or shares sequence identity with a gene that is known to have at least one characteristic that involves a process associated with cell proliferation, transformation, or tumorigenesis. As non-limiting examples, the gene can be known to have at least one of the following characteristics, or known to be a member of a family of genes that have at least one of the following characteristics:

a) mitotically regulated;
b) a regulator of chromosome segregation and cytokinesis;
c) expression at certain phases of the cell cycle;
d) amplified in at least one tumor type; and
e) over expressed in at least one cancer type;

In another aspect, the present invention provides a method for identifying a low penetrance tumor susceptibility gene or allele, by identifying allele-specific loss. In these embodiments, the tumor susceptibility allele can be retained. Methods are known in the art for identifying loss of an allele, including those described herein for detecting amplification.

In another aspect, the present invention provides an isolated polynucleotide comprising at least 10, 25, 30, 50, 100, 125, 250, 500, 1000, 1500, 2000, 2100, 2200, 2253, 2347 etc. nucleotides derived from the human STK15 gene, that includes an adenosine at a position corresponding to nucleotide 457 of SEQ ID NO:1. In certain embodiments, the polynucleotide includes the entire mRNA (Genbank NM003600), or a cDNA derived therefrom, of the human STK15 gene, wherein an adenosine residue is found at a position corresponding to nucleotide 457 of SEQ ID NO:1.

The polynucleotides of the present invention have many uses. For example, the polynucleotides can be used in recombinant DNA technologies to produce recombinant polypeptides that can be used, for example, to identify test agents, such as small organic compounds, that effect the kinase activity of STK15. Furthermore, the polynucleotides can be used to develop test agents that bind to the polynucleotides and inhibit the translation of the polynucleotides into polypeptides.

Accordingly, the present invention also provides an isolated polypeptide that is encoded by an isolated polynucleotide of the present invention, that includes at least 10, 25, 50, 100, 150, 200, 400, 403, etc. consecutive amino acids of SEQ ID NO:2, wherein one of the amino acids corresponds to an isoleucine residue at position 31 of SEQ ID NO:2. SEQ ID NO:2 provides the amino acid sequence of the polypeptide encoded by the STK15 gene. The Ile 31 polypeptide encoded by the STK15 Ile31 polymorphic variant identified herein as associated with increased susceptibility to cancer, includes an isoleucine reside at position 31 of SEQ ID NO:2. The polypeptide can include the entire polypeptide of SEQ ID NO:2. The isolated polypeptide can be used to identify test agents that inhibit the activity of STK15, inhibit cell proliferation, inhibit tumor formation, or inhibit cancer formation.

In another aspect, the present invention provides an isolated polynucleotide that includes at least 10, 25, 50, 100, 150, 200, 250, 500, etc. consecutive nucleotides of a gene that includes the SNPs of Table 3 herein, preferably, the SNPs that were not previously reported in a public database. Most preferably the polynucleotide includes a minor nucleotide occurrence reported herein. Accordingly, the present invention also provides isolated polypeptides encoded by the isolated polynucleotides disclosed above.

The present invention also provides an isolated human cell or an isolated plurality of cells, which contain an endogenous STK15 gene with an adenosine residue at a position corresponding nucleotide 457 of SEQ ID NO:1. Preferably, the isolated human cell is homozygous for the adenosine residue at a position corresponding to nucleotide 457 of SEQ ID NO:1. The cell can include an adenosine residue at a position corresponding to nucleotide 457 of SEQ ID NO:1, on each copy of chromosome 20 or amplification product thereof. The STK15 gene can be amplified, and the STK15 Ile polymorphism can be selectively amplified in the isolated cell. The isolated cell can be derived from a cell line, or can be a primary cell, or a passaged primary cell.

In another embodiments, the present invention provides an isolated human cell or an isolated plurality of cells, that include a minor occurrence of a SNP of Table 3, especially a SNP that was not previously reported in a public database.

In another aspect, the present invention provides a plurality of enriched populations of isolated human cells that include a first population of human cells comprising an endogenous STK15 gene comprising an adenosine residue at a position corresponding to nucleotide 457 of SEQ ID NO:1; and at least a second population of human cells comprising an endogenous STK15 gene comprising a thymidine residue at a position corresponding to nucleotide 457 of SEQ ID NO:1. This aspect of the invention includes at least two (e.g., 2, 3, 4, 5, 6, 7, 8, or more) populations of cells. The first population of human cells can include an adenosine residue at a position on each copy of chromosome 20 or amplification product thereof, corresponding to nucleotide 457 of SEQ ID NO:1. That is, the first population can be homozygous for the STK15 Ile31 polymorphism. One or more of the populations of cells can include STK15 gene amplification, including STK15 Ile31 selective amplification.

As illustrated in the Examples section, isolated cells that are homozygous for adenosine at the STK15 Ile31 allele (nucleotide 457 of SEQ ID NO:1) are expected to have an increased chance of developing properties associated with cancer, (e.g. a transformed phenotype), since subjects with this polymorphism have an increased cancer susceptibility. Therefore, isolated cells that include homozygous STK15 Ile31 alleles, are useful for identifying test agents that can inhibit cell proliferation, inhibit tumor formation, inhibit cancer formation, and/or treat cancer.

Accordingly, in another aspect, the present invention provides a method for identifying a test agent which affects STK15 activity, or an aspect of a process related to a transformed phenotype and/or related to cancer formation. The method includes contacting an isolated cell of the invention with the test agent, and analyzing STK15 activity in the isolated cell, or analyzing the cell for a process related to a transformed or immortalized phenotype and/or related to cancer formation. Such processes are known in the art, and include for example, cell division, cellular morphology, cell senescence, apoptosis, chromosome amplification, chromosomal instability, etc. Accordingly, the method of this aspect of the invention is a method of identifying a test agent that inhibits cell division, inhibits cell proliferation, affects cellular morphology, affects senescence, affects apoptosis, inhibits chromosome amplification, and promotes chromosome stability.

The test agent can affect any STK15 activity, including STK15 kinase activity. The test agent in certain embodiments, is a small organic compound, or in other embodiments, as a non-limiting example, an antibody.

A method of identifying a test agent can be performed, for example, by contacting an isolated cell of the present invention with at least a test agent to be examined as a potential agent for treating cancer or a cell proliferative disorder, under appropriate conditions. Before exposure to a target agent, the isolated cell can be analyzed for a process related to a transformed or immortalized phenotype and/or related to cancer formation, STK15 activity or expression of STK15 Ile31. These results can be compared to enzyme activity or expression levels after exposure to a test agent. Furthermore, such results obtained using cells with an STK15 Ile31 allele, or preferably homozygous STK15 Ile31 alleles, can be compared to results under similar conditions obtained for cells having an STK15 F31 allele, including heterozygous cells that include both an STK15 F31 and STK15 Ile31 allele. A difference in results between the STK15 Ile31 cells and those homozygous for STK15 F31, indicates that the test compound is a potentially useful for the treatment of cancer.

The term "test agent" is used herein to mean any agent that is being examined for the ability to affect STK15 (STK6) activity, or a process related to a transformed phenotype and/or related to cancer formation. The method generally is used as a screening assay to identify previously unknown molecules that can act as therapeutic agents for treating cancer.

A test agent can be any type of molecule, including, for example, a peptide, a peptidomimetic, a polynucleotide, or a small organic molecule, that one wishes to examine for the ability to act as a therapeutic agent, which is a agent that provides a therapeutic advantage to a subject receiving it. It will be recognized that a method of the invention is readily adaptable to a high throughput format and, therefore, the method is convenient for screening a plurality of test agents either serially or in parallel. The plurality of test agents can be, for example, a library of test agents produced by a combinatorial method library of test agents. Methods for preparing a combinatorial library of molecules that can be tested for therapeutic activity are well known in the art and include, for example, methods of making a phage display library of peptides, which can be constrained peptides (see, for example, U.S. Pat. No. 5,622,699; U.S. Pat. No. 5,206,347; Scott and Smith, *Science* 249:386–390, 1992; Markland et al., *Gene* 109:13–19, 1991; each of which is incorporated herein by reference); a peptide library (U.S. Pat. No. 5,264,563, which is incorporated herein by reference); a peptidomimetic library (Blondelle et al., *Trends Anal. Chem.* 14:83–92, 1995; a nucleic acid library (O'Connell et al., supra, 1996; Tuerk and Gold, supra, 1990; Gold et al., supra, 1995; each of which is incorporated herein by reference); an oligosaccharide library (York et al., *Carb. Res.,* 285:99–128, 1996; Liang et al., *Science,* 274:1520–1522, 1996; Ding et al., *Adv. Expt. Med. Biol.,* 376:261–269, 1995; each of which is incorporated herein by reference); a lipoprotein library (de Kruif et al., *FEBS Lett.,* 399:232–236, 1996, which is incorporated herein by reference); a glycoprotein or glycolipid library (Karaoglu et al., *J. Cell Biol.,* 130:567–577, 1995, which is incorporated herein by reference); or a chemical library containing, for example, drugs or other pharmaceutical agents (Gordon et al., *J. Med. Chem.,* 37:1385–1401, 1994; Ecker and Crooke, *Bio/Technology,* 13:351–360, 1995; each of which is incorporated herein by reference). Accordingly, the present invention also provides a therapeutic agent identified by such a method, for example, a cancer therapeutic agent.

Assays that utilize these cells to screen test agents are typically performed on isolated cells of the present invention in tissue culture. The isolated cells can be cells from a cell line, passaged primary cells, or primary cells, for example. An isolated cell according to the present invention can be, for example, a cell derived from a colon tumor or a breast tumor.

A screening method of the invention also can be performed using the methods of molecular modeling as described above. The utilization of a molecular modeling method provides a convenient, cost effective means to identify those agents, among a large population such as a combinatorial library of potential agents, that are most likely to interact specifically with STK15 (STK6), thereby reducing the number of potential agents that need to be screened using a biological assay. Upon identifying agents that interact specifically with a STK15 (STK6) using a molecular modeling method, the selected agents can be examined for the ability to modulate an effect STK15 (STK6), such as STK15 (STK6) kinase activity.

The ability of a test agent to modulate an effect of STK15 (STK6) can be detected using methods as disclosed herein or otherwise known in the art. The term "test agent" or "test molecule" is used broadly herein to mean any agent that is being examined for agonist or antagonist activity in a method of the invention. Although the method generally is used as a screening assay to identify previously unknown molecules that can act as agonist or antagonist agents as described herein, the methods also can be used to confirm that a agent known to have a particular activity in fact has the activity, for example, in standardizing the activity of the agent.

A screening method of the invention provides the advantage that it can be adapted to high throughput analysis and, therefore, can be used to screen combinatorial libraries of test agents in order to identify those agents that can modulate an effect of STK15 (STK6) on a cell. Methods for preparing a combinatorial library of molecules that can be tested for a desired activity are well known in the art and include, for example, methods of making a phage display library of peptides, which can be constrained peptides (see, for example, U.S. Pat. No. 5,622,699; U.S. Pat. No. 5,206,347; Scott and Smith, *Science* 249:386–390, 1992; Markland et al., *Gene* 109:13–19, 1991; each of which is incorporated herein by reference); a peptide library (U.S. Pat. No. 5,264,563, which is incorporated herein by reference); a peptidomimetic library (Blondelle et al., *Trends Anal. Chem.* 14:83–92, 1995); a nucleic acid library (Connell et al., supra, 1996; Tuerk and Gold, supra, 1990; and Gold et al., supra, 1995; each of which is incorporated herein by reference); an oligosaccharide library (York et al., *Carb. Res.,* 285:99–128, 1996; Liang et al., *Science,* 274:1520–1522, 1996; Ding et al., *Adv. Expt. Med. Biol.,* 376:261–269, 1995; each of which is incorporated herein by reference); a lipoprotein library (de Kruif et al., *FEBS Lett.,* 399:232–236, 1996, which is incorporated herein by reference); a glycoprotein or glycolipid library (Karaoglu et al., *J. Cell Biol.,* 130:567–577, 1995, which is incorporated herein by reference); or a chemical library containing, for example, drugs or other pharmaceutical agents (Gordon et al., *J. Med. Chem.,* 37:1385–1401, 1994; Ecker and Crooke, *Bio/Technology,* 13:351–360, 1995; each of which is incorporated herein by reference).

In another embodiment the present invention provides a vector containing one or more of the isolated polynucleotides disclosed herein. Many vectors are known in the art, including expression vectors. In one aspect, the vectors of the present invention include an isolated polynucleotide of the present invention that encodes a polypeptide, operatively linked to an expression control sequence such as a promoter sequence on the vector. Sambrook (1989) for example, provides examples of vectors and methods for manipulating vectors, which are well known in the art.

In another embodiment, the present invention provides an isolated cell containing one or more of the isolated polynucleotides disclosed herein, or one or more of the vectors disclosed in the preceding sentence. As such, the cell is a recombinant cell.

The present invention in another aspect provides, an isolated primer pair wherein a forward primer selectively binds a polynucleotide upstream of an adenosine residue at a position corresponding to the adenosine position on one strand and a reverse primer selectively binds the polynucleotide upstream of a thymidine position, wherein the thymidine residue is complementary to the adenosine residue on a complementary strand of the polynucleotide. The 3' nucleotide of the primer can be complementary to the adenosine. The forward primer and the reverse primer can selectively bind to SEQ ID NO:1, or a complementary strand thereof. The forward primer, in one preferred embodiment is 5'-TTCCATTCTAGGCTACAGCTCCA-3, (SEQ ID NO:23), and the reverse primer in a preferred embodiments is 5'-CAAGACCCGCTGAGCCTG-3, (SEQ ID NO:24).

In another aspect the isolated primer pair can include a forward primer and reverse primer as discussed above, wherein the primers can be used to amplify a SNP of Table 3, especially a SNP of Table 3 that was not previously reported in a public database.

In another aspect, the present invention provides an isolated probe for determining a nucleotide occurrence of a position corresponding to nucleotide 457 of SEQ ID NO:1, wherein the probe selectively binds to a polynucleotide comprising an adenosine residue or selectively binds to a polynucleotide comprising a thymidine residue, at the position corresponding to nucleotide 457 of SEQ ID NO:1. For example, the probe can selectively bind to any all or any portion of the STK15 gene or a transcript derived therefrom, for example the probe can bind to all, or any portion of the entire polynucleotide of SEQ ID NO:1. In certain preferred embodiments, the probe can include an STK15 AA31-"A"

probe: 5'-6FAM-CTCAGCAAATTCCTTGTCAG-MGBNFQ-3, (SEQ ID NO:25), or an STK15 AA31-"T" probe: 5'-VIC-CTCAGCAATTTCCTTGTCAG-MGBNFQ-3 (SEQ ID NO:26).

In another aspect, the present invention provides an isolated primer for extending a polynucleotide comprising an adenosine at a position corresponding to nucleotide 457 of SEQ ID NO:1, wherein the primer selectively binds upstream of the position on one strand, and selectively primes an extension reaction when the adenosine residue is present. For example, such a primer can be used for a primer extension reaction using the Orchid SNPit™ technology (Orchid Biosciences, Princeton N.J.).

In another aspect, the present invention provides an isolated primer pair or probe as generally describe above, but wherein the probe or primer are targeted to a SNP of Table 3, preferably a SNP of Table that was previously not included in a database (as indicated in Table 3).

In a related aspect to the probe aspect above, the present invention provides an isolated specific binding pair member for determining a nucleotide occurrence at a position corresponding to nucleotide 457 of SEQ ID NO:1 in a polynucleotide, wherein the specific binding pair member specifically binds at or near an adenosine residue at a position corresponding to nucleotide 457 of SEQ ID NO:1. The specific binding pair member can be, as non-limiting examples, a polynucleotide probe., for example that includes the nucleotide sequence of SEQ ID NO25 or SEQ ID NO:26, an antibody, a substrate for a primer extension reaction, for example where the substrate selectively binds to a polynucleotide corresponding to all or a portion of the STK15 gene that includes the STK15 F31I SNP as its terminal nucleotide. Such specific binding pair members can be designed to be successfully employed as a substrate for a primer extension reaction, only when certain nucleotides, such as an adenosine or thymidine, are present.

For methods wherein the specific binding pair member is a substrate for a primer extension reaction, the specific binding pair member is a primer that binds to a polynucleotide at a sequence comprising the STK15 F31I SNP as the terminal nucleotide. As discussed above, methods such as SNP-IT™ (Orchid BioSciences), utilize primer extension reactions using a primer whose terminal nucleotide binds selectively to certain nucleotide occurrence(s) at a SNP loci, to identify a nucleotide occurrence at the SNP loci.

In addition, the present invention relates to a method for detecting a nucleotide occurrence for a SNP in a polynucleotide by incubating a sample containing the polynucleotide with a specific binding pair member, wherein the specific binding pair member specifically binds at or near a polynucleotide suspected of being polymorphic, and wherein the polynucleotide includes an adenosine residue at nucleotide 457 of SEQ ID NO:1, wherein selective binding is indicative of the presence of the nucleotide occurrence. Such methods can be performed, for example, by a primer extension reaction or an amplification reaction such as a polymerase chain reaction, using an oligonucleotide primer that selectively hybridizes upstream, or an amplification primer pair that selectively hybridizes to nucleotide sequences flanking and in complementary strands of the SNP position, respectively; contacting the material with a polymerase; and identifying a product of the reaction indicative of the SNP. Methods according to this aspect of the invention can be used for example, to determine cancer risk for an individual, or for fingerprint analysis, to identify an individual.

In another aspect, the present invention provides a method for determining cancer susceptibility of a mammalian subject by determining expression of the STK15 Ile31 polymorphism in a sample of the mammalian subject, wherein over-expression of the STK15 Ile31 allele indicates an increased cancer risk, thus providing a determination of cancer susceptibility of the mammalian subject. The subject can be a mammal, for example a human or a murine species. Expression can be determined by analyzing RNA or proteins of the sample of the mammalian subject. The sample can include breast cells, colon cells, or skin cells, and/or cancer cells. Over-expression can be identified by comparing STK15 expression in the sample to expected STK15 expression in a sample from a wild-type subject. The wild-type subject can be, for example, a subject with an STK15 Phe31 polymorphism.

Immunohistochemical analyses revealed overexpression of STK15 in 94% of invasive ductal adenocarcinomas of the breast, which is intriguing since genetic instability is an early event in the development of ductal breast carcinoma (Tanaka, T. et al., Cancer Res. 59, 2041–2044 (1999); and Romanov, S. R. et al., Nature 409, 633–637 (2001)). The present invention, discloses that the human STK15 Ile31 allele is selectively amplified, and that in mice, selective amplification of an STK15 allele can be associated with overexpression. Many methods are known in the art for determining expression. Typically, as is known in the art, such methods involve isolating proteins or ribonucleic acids (RNA) from a sample, separating isolated proteins or nucleic acids, and detecting an RNA or protein of interest. Any method known in the art for determining expression, for example, Northern blot, western blot, ELISA, PCR, etc. can be used with the present invention. Useful for such methods, are the specific binding members, such as probes, primers, primer pairs, and antibodies disclosed herein.

In another aspect, the present invention provides a method for inhibiting expression of STK15 that includes contacting a mammalian cell with a reagent that inhibits expression of STK15, preferably the STK15 Ile31 allele. In certain preferred embodiments, the mammalian cell has two or more endogenous STK15 Ile31 alleles. Many methods are known in the art for inhibiting gene expression, and which could be used with the present invention. For example, the method can utilize an antisense oligonucleotide, that selectively binds to an STK15 polynucleotide.

An agent useful in a method of this aspect of the invention can be a polynucleotide, which can be contacted with or introduced into a cell using methods known in the art. Generally, but not necessarily, the polynucleotide is introduced into the cell, where it effects its function either directly, or following transcription or translation or both. For example, the polynucleotide can encode a peptide agent, which is expressed in the cell and modulates STK15 activity.

A polynucleotide agent useful in a method of the invention also can be, or can encode, an antisense molecule, a ribozyme or a triplexing agent. Such polynucleotides can be contacted directly with a target cell and, upon uptake by the cell, can effect their antisense, ribozyme or triplexing activity; or can be encoded by a polynucleotide that is introduced into a cell, whereupon the polynucleotide is expressed to produce, for example, an antisense RNA molecule or ribozyme, which effects SSTK6 activity.

An antisense polynucleotide, ribozyme or triplexing agent is complementary to a target sequence, which can be a DNA or RNA sequence, for example, messenger RNA, and can be a coding sequence, a nucleotide sequence comprising an intron-exon junction, a regulatory sequence such as a Shine-Delgarno sequence, or the like. The degree of complementarity is such that the polynucleotide, for example, an antisense polynucleotide, can interact specifically with the target sequence in a cell. Depending on the total length of the antisense or other polynucleotide, one or a few mismatches with respect to the target sequence can be tolerated without losing the specificity of the polynucleotide for its target sequence. Thus, few if any mismatches would be tolerated in an antisense molecule consisting, for example, of 20 nucleotides, whereas several mismatches will not affect the hybridization efficiency of an antisense molecule that is complementary, for example, to the full length of a target mRNA encoding a cellular polypeptide. The number of mismatches that can be tolerated can be estimated, for example, using well known formulas for determining hybridization kinetics (see Sambrook et al., supra, 1989) or can be determined empirically using methods as disclosed herein or otherwise known in the art, particularly by determining that the presence of the antisense polynucleotide, ribozyme, or triplexing agent in a cell decreases the level of the target sequence or the expression of a polypeptide encoded by the target sequence in the cell.

A polynucleotide useful as an antisense molecule, a ribozyme or a triplexing agent can inhibit translation or cleave the nucleic acid molecule, thereby modulating STK15 activity, such as STK15 kinase in a cell. An antisense molecule, for example, can bind to an mRNA to form a double stranded molecule that cannot be translated in a cell. Antisense oligonucleotides of at least about 15 to 25 nucleotides are preferred since they are easily synthesized and can hybridize specifically with a target sequence, although longer antisense molecules can be expressed from a polynucleotide introduced into the target cell. Specific nucleotide sequences useful as antisense molecules can be identified using well known methods, for example, gene walking methods (see, for example, Seimiya et al., *J. Biol. Chem.* 272:4631–4636 (1997), which is incorporated herein by reference). Where the antisense molecule is contacted directly with a target cell, it can be operatively associated with a chemically reactive group such as iron-linked EDTA, which cleaves a target RNA at the site of hybridization. A triplexing agent, in comparison, can stall transcription (Maher et al., *Antisense Res. Devel.* 1:227 (1991); Helene, *Anticancer Drug Design* 6:569 (1991)).

In another aspect, the present invention provides a method for inhibiting growth of a mammalian cancer cell by contacting the mammalian cancer cell with a reagent that inhibits STK15 (STK6) activity. The reagent can inhibit, for example, STK15 (STK6) kinase activity. In preferred embodiments, the cancer cell includes one, or more preferably two or more, STK15 Ile31 alleles. The reagent can be, for example, an antibody, or a kinase inhibitor.

As indicated above, studies of cancer predisposition have largely concentrated on the role of high penetrance susceptibility genes. Less than 10% of the total human tumor burden, however, is accounted for by mutations in these genes (Ponder, B. A. J., *Nature* 411, 336–341 (2001). More genetic variation in cancer risk is likely to be due to commoner but lower penetrance alleles (Ponder, B. A. J., *Nature* 411, 336–341 (2001); and Balmain, A., *Trends Genet.* 14, 139–144 (1998)). In man, such genes are difficult to find since they do not segregate as single Mendelian traits.

The mouse offers a powerful system for studying polygenic traits such as cancer and has been widely used for this purpose (Dietrich, W. F. et al., *Cell* 75, 631–639 (1993); Fijneman, R., et al., *Nature Genet.* 14, 465–467 (1996); van Wezel, T. et al., *Nature Genet.* 14, 468–470 (1996); Nagase, H. et al., *Nature Genet.* 10, 424–429 (1995); Nagase, H., et al., *Proc. Natl. Acad. Sci. USA* 96, 15032–15037 (1999)). However, major problems need to be overcome at several levels in any strategy to find tumor modifier genes: mapping the locus at high resolution, identifying the critical gene, and finding the functional polymorphism. Standard linkage analysis methods for localizing quantitative trait loci (QTLs) detect loci within intervals of at least 10 to 30 cM, and the usual method of refining the region involves generation of congenic mice. This is an expensive and time-consuming process that can experience problems due to co-localization of multiple QTLs within the same interval, or because of the presence of interacting genes necessary for the phenotype. Finally, identification of the critical polymorphism is difficult because all of the genes in the immediate vicinity will exhibit sequence variants that correlate with the phenotype.

The present invention, in one aspect provides a novel multi-step approach that helps to resolve many of these problems by exploiting the genetic diversity between tumor-susceptible organisms and tumor-resistant strains of an organism or species of the same genus, such as different mouse strains, together with the high recombination and low linkage disequilibrium found in humans. As will be recognized, when different species are employed in the crosses used for the present invention, such as different mouse species, the species must be capable of yielding viable progeny when crossed.

Accordingly, in another aspect, the invention provides a method for identifying genes as low penetrance tumor susceptibility genes. This aspect of the invention provides commercially valuable research tools, for example. The approach can be performed generally as follows:

First, one or more general genetic loci involved in tumor susceptibility are identified by crossing a first organism of a first strain of a first non-human mammalian species of a first genus with a second organism of either a second strain of the first non-human mammalian species or a first strain of a second non-human mammalian species of the first genus. The second organism has a different tumor susceptibility than the first organism. The genomes of progeny are correlated with different tumor susceptibility. To assist in the identification, backcrossing can be performed.

Next, a more finely mapped genetic locus involved in tumor susceptibility, found within the one or more general genetic loci, is identified by analyzing cancer correlation of haplotypes of the general genetic loci. As will be recognized, haplotypes are a series of genetic markers that are located on the same region of a chromosome, which can be compared to identify subregions which are linked to a trait, such as cancer susceptibility. The involvement of the more finely mapped genetic locus with cancer, can be confirmed using linkage analysis. As will be recognized, linkage analysis identifies genetic markers that segregate with a trait, using genetic analysis.

Then, a candidate human gene on a target human genome locus is identified, that is orthologous to the more finely mapped locus. Next, alleles in the candidate human gene that exhibit different genotype frequencies between normal healthy controls and subjects having cancer are identified. In certain embodiments, the first and second non-human mammalian species are rodent species, in certain preferred embodiments, mouse species. For example, the first organism can be *Mus spretus* and the second organism can be *Mus musculus*. Tumor-susceptible strains of *Mus musculus* and tumor resistant strains of *Mus spretus* are known in the art, and available commercially (The Jackson Laboratory, Bar Harbor, Me.).

This aspect of the invention is illustrated, in a non-limiting manner, in the Example section herein. Furthermore, a preferred embodiment of this aspect of the invention is illustrated in FIG. 5.

In certain preferred embodiments, the first organism is from an inbred strain and the second organism is from an outbred strain.

For example, in a preferred embodiment, the first organism is the tumor-susceptible *Mus musculus*, and the second organism is an outbred or inbred strain of tumor-resistant *Mus spretus*. In certain preferred embodiments, the *Mus musculus* is crossed with both outbred and inbred strains of *Mus spretus*. The mouse can include inbred SEG/Pas (derived from *Mus spretus*), inbred NIH/Ola, or inbred SPRET/Ei (Jackson Laboratory). For example, the initial cross can be a series of crosses between inbred NIH/Ola and the following: outbred *Mus spretus*, inbred SEG/Pas, and inbred SPRET/Ei. Backcrosses can then be performed between the progeny of the initial series of crosses and NIH/Ola. In these specific examples, tumor susceptibility is typically determined by inducing skin tumors using the same protocol, as are known in the art, and estimating cancer susceptibility by determining the number of papillomas that develop after a set period, for example 20 weeks, after tumor initiation.

Genotyping can be performed using microsatellite marker analysis. Where mice are used, marker positions can be based on the Mouse Genome Database (available at www.informatics.jax.org). Linkage analysis can be performed by identifying QTLs using for example negative binomial regression analysis (Nagase, H., et al., *Proc. Natl. Acad. Sci. USA*, 96, 15032–15037 (1999), incorporated herein by reference in its entirety; Cormier, R. T. et al., *Oncogene* 19, 3182–3192 (2000), incorporated herein by reference in its entirety; and Balmain, A., *Cell* 108, 145–152 (2002), incorporated herein by reference in its entirety), as discussed in more detail below, as a non-limiting example.

Microsatellite markers with an average genomic spacing, for example of about 10 centimorgans (cM) can be employed using DNA isolated using standard methods. Tumor multiplicity in chemical carcinogen-induced mouse experiments frequently follows a negative binomial distribution (Drinkwater, N., et al., *Cancer Res.*, 41, 113 (1981); ), especially when the tumor number is overdispersed, such as in the *Mus spretus/Mus musculus* backcross, where more than 30% of animals have no papilloma. For QTL analysis, tumor multiplicity data are generally transformed by root-square transformation to improve the fit of negative binomial data to a normal distribution (Drinkwater N., et al., (1981)) or alternatively are analyzed by using a nonparametric test (Kruglyak, L., *Genetics* 139, 1421 (1995)). However, transformation does not improve the analysis substantially in a case with overdispersion. Normally a nonparametric test is less powerful than a parametric test when the data are fit to a standard distribution. Because papilloma multiplicity data fitted very well to a negative binomial distribution by testing for goodness of fit (Kendall *Advanced Theory of Statistics* (Hafner, N.Y.)), a negative binomial multiple regression analysis can be employed to screen for predisposition loci associated with papilloma multiplicity.

The negative binomial regression model is $$Pr\{Y=N\}=\{\Gamma(N+q)/[\Gamma(N+1)\Gamma(\theta)]\}\times\{\theta/[\theta+\mu(X)]\}^\theta\{\mu(X)/[\theta+\mu(X)]\}^N, \qquad [1]$$

where Y is number of papillomas and indicates the heterogeneity of response, $$\mu(X) = e^{\{\Sigma_i a_i x_i + \Sigma_i \Sigma_j b_{ij} x_i^* x_j\}} \qquad [2]$$

is the mean, and $x_i$ is the value of marker I. $x_i$ is 1 if marker I is homozygous. $x_i$ is 0 if marker I is heterozygous.

Stepwise negative binomial regression analysis can be analyzed, for example using STATA (Stata, College Station, Tex.).

The association between carcinoma incidence and marker can be analyzed by a logistic regression method as described Nagase, H., et al., *Nat. Genet.* 10, 424 (1995). Cox multiple regression analysis, which is a multivariate analysis technique (Cox, D. R., *Stat Soc.* 34, 187 (1972); and Cox et al., Analysis of Survival Data (Chapman& Hall, London) (1984)), can be used to detect the effect of multiple genotypes on papilloma onset and survival after carcinoma development. The combined effect of the loci can be screened genome-wide by stepwise Cox regression analysis (STATA, Stata, College Station, Tex.). The statistical estimation of relationships between cancer grade and genotype can be calculated by using a Trend test (STATA, Stata, College Station, Tex.; Fleiss, J. L., Statistical Methods for Rates and Proportions (Wiley, N.Y.), 2nd Ed. (1981)).

For haplotype analysis, specific haplotypes can be grouped for a particular trait, such as tumor formation, and comparison of the grouped haplotypes can reveal markers that are linked to the trait.

Published data and on-line internet resources can be used to find orthologous regions of the human genome to genomic regions of non-human species such as mice. (See e.g., www.ncbi.nlm.nih.gov/Homology/; Hudson, T. J., et al., *Nat Genet* 2:201–5 (2001)). Alleles in the candidate human gene that exhibit different genotype frequencies between normal healthy controls and subjects having cancer are identified using standard statistical analysis, as disclosed herein for the discovery of the STK15 Ile31 allele.

The invention also relates to kits, which can be used, for example, to perform a method of the invention. Thus, in one embodiment, the invention provides a kit for identifying a nucleotide occurrence at a position corresponding to nucleotide 457 of SEQ ID NO:1. The kit can include an isolated primer, primer pair, probe, or other specific binding pair member of the present invention., or a combination thereof. The kit can further include reagents for amplifying a polynucleotide using a primer pair. Furthermore, the reagents can include at least one detectable label, which can be used to label the isolated oligonucleotide probe, primer, primer pair, or other specific binding pair member, or can be incorporated into a product generated using the isolated oligonucleotide probe, primer, primer pair, or specific binding pair member. The kit can also include at least one polymerase, ligase, or endonuclease, or a combination thereof. The kit can further include at least one polynucleotide corresponding to a portion of an STK15 gene comprising a position corresponding to nucleotide 457 of SEQ ID NO:1. In one embodiment, the kit includes an isolated probe, and an isolated primer pair of the present invention, as described above.

The kit can also include an isolated polynucleotide or isolated antibody according to the present invention, which can be useful, for example, as a standard (control) that can be examined in parallel with a test sample.

In addition, a kit of the invention can contain, for example, reagents for performing a method of the invention, including, for example, one or more detectable labels, which can be used to label a probe or primer or can be incorporated into a product generated using the probe or primer (e.g., an amplification product); one or more polymerases, which can be useful for a method that includes a primer extension or amplification procedure, or other enzyme or enzymes (e.g., a ligase or an endonuclease), which can be useful for performing an oligonucleotide ligation assay or a mismatch cleavage assay; and/or one or more buffers or other reagents that are necessary to or can facilitate performing a method of the invention. The primers or probes can be included in a kit in a labeled form, for example with a label such as biotin or an antibody.

In one embodiment, a kit of the invention includes one or more primer pairs of the invention, such a kit being useful for performing an amplification reaction such as a polymerase chain reaction (PCR). Such a kit also can contain, for example, one or reagents for amplifying a polynucleotide using a primer pair of the kit. The primer pair(s) can be selected, for example, such that they can be used to determine the nucleotide occurrence of a polynucleotide of a sample, at a position corresponding to nucleotide 457 of SEQ ID NO:1, wherein a forward primer of a primer pair selectively hybridizes to a sequence of the target polynucleotide upstream of the SNP position on one strand, and a reverse primer of the primer pair selectively hybridizes to a sequence of the target polynucleotide upstream of the SNP position on a complementary strand. When used together in an amplification reaction an amplification product is formed that includes the SNP loci.

In addition to primer pairs, in this embodiment the kit can further include a probe that selectively hybridizes to the amplification product of one of the nucleotide occurrences of the STK15 F31I SNP, but not the other nucleotide occurrence. Also in this embodiment, the kit can include a third primer which can be used for a primer extension reaction across the SNP loci using the amplification product as a template. In this embodiment the third primer preferably binds to the SNP loci such that the nucleotide at the 3' terminus of the primer is complementary to one of the nucleotide occurrences at the SNP loci. The primer can then be used in a primer extension reaction to synthesize a polynucleotide using the amplification product as a template, preferably only where the nucleotide occurrence is complementary to the 3' nucleotide of the primer. The kit can further include the components of the primer extension reaction.

In another embodiment, a kit of the invention provides a plurality of oligonucleotides of the invention, including one or more oligonucleotide probes or one or more primers, including forward and/or reverse primers, or a combination of such probes and primers or primer pairs. Such a kit provides a convenient source for selecting probe(s) and/or primer(s) useful for identifying one or more SNPs or haplotype alleles as desired. Such a kit also can contain probes and/or primers that conveniently allow a method of the invention to be performed in a multiplex format.

The kit can also include instructions for using the probes or primers to perform a method of the present invention.

The following examples are intended to illustrate but not limit the invention.

EXAMPLE 1

Identification of STK15 (STK6) as a Low Penetrance Tumor Susceptibility Gene This example illustrates the use of mouse genetics and human population studies to map a low penetrance tumor susceptibility gene, the STK15 (STK6) gene, and a cancer-associated allele of that gene, the STK15 Ile31 allele. The mouse genetics studies included linkage analysis and haplotyping.

Methods

Mice and tumor induction. Inbred NIH/Ola mice were purchased from Harlan Olac (Bichester, United Kingdom). Outbred *Mus spretus* and inbred SEG/Pas (derived from *Mus spretus*) were obtained from Drs. S. Brown (Medical Research Council, Harwell, UK) and Jean-Louis Guenet (Institute Pasteur, Paris, France), respectively. Inbred SPRET/Ei mice were purchased from The Jackson Laboratory. Three backcrosses were performed with these different *Mus spretus* strains: NSP, (NIH/Ola×outbred *Mus spretus*)× NIH/Ola; NSE, (NIH/Ola×inbred SEG/Pas)×NIH/Ola; and NSJ, (NIH/Ola×inbred SPRET/Ei)×NIH/Ola. In these crosses the same breeding and skin tumor induction protocols were carried out, and papilloma susceptibility was estimated by the number of papillomas at 20 weeks after initiation in 320 NSP, 163 NSJ, and 106 NSE mice, as reported previously (Nagase, H., et al., *Proc. Natl. Acad. Sci. USA* 96, 15032–15037 (1999); Bremner, R., et al., *Mol. Carcinog.* 11, 90–97 (1994)).

Mouse genotyping, linkage analysis, and haplotyping. DNAs were prepared from tails and amplified by standard methods. Mice were genotyped by using microsatellite markers. Marker positions given are based on the Mouse Genome Database (http://www.informatics.jax.org). Negative binomial regression analysis was used to identify QTLs that control skin tumor susceptibility, as reported previously (Nagase, H., et al., *Proc. Natl. Acad. Sci. USA* 96, 15032–15037 (1999); Cormier, R. T. et al., *Oncogene* 19, 3182–3192 (2000); and Balmain, A., *Cell* 108, 145–152 (2002)). For fine mapping of QTLs, haplotypes in outbred *Mus spretus* mice were constructed for association studies by using the variation in length of microsatellites between the different NSP alleles.

SNP identification. Primers for PCR were designed from the published and database sequences of CYP24, ZNF217, and STK15 (STK6). Automated sequencing of PCR products was conducted on an ABI 3700 by standard methods. Sequences were analyzed using Sequencher™ (Genes Codes Corporation, Ann Arbor, Mich.). Sequence discrepancies were confirmed by reverse reads and RFLP analysis where possible.

Human Study Populations. For hypothesis generation and confirmation the case-control population samples were examined as separate series (strata; English and Finnish populations). The East Anglican British cases (n=1944) were drawn from the Anglican Breast Cancer Study cancer. All patients diagnosed below age 55 years since 1991 and alive in 1996 (prevalent cases, median age 48 years), together with all those under 65 years diagnosed between 1996 and present (incident cases, median age 52), were eligible. Controls were randomly selected from the UK part of the European Prospective Investigation of Cancer (EPIC) (Riboli, E., *Ann. Oncol.*, 3, 783–791 (1992); and Day, N. et al., *Br. J. Cancer* 80, Suppl. 1, 95–103 (1999)).

The relevant local research ethics committees approved these studies. All participants provided written consent, completed an epidemiological questionnaire and provided a blood sample. The ethnic background of both cases and controls is similar, with over 99% being white Anglo-Saxon. No evidence for population stratification was seen in controls. Finnish individuals collected from a population-based, case-control study from the Kuopio Breast Cancer Project (KBCP) were used as a second population to study any positive findings. Blood samples were collected from women with any suspected breast disease who came to Kuopio University Hospital for breast examination between April 1990 and December 1995. For this study 498 female breast cancer patients were included as cases. Controls (n=461) were randomly selected and individually matched for age (within 5 years) and area-of-residence from the National Population Register for each case of breast cancer. The joint ethics committee of Kuopio University and Kuopio University Hospital approved the KBCP. Each patient gave informed written consent for participation in the study.

Human genotyping analyses. All SNPs for the association studies were genotyped using the ABI PRISM 7700 sequence detection system (Applied Biosystems, Foster City, Calif.). PCR reactions contained genomic DNA (4–10 ng), 1×TaqMan universal PCR master mix, forward and reverse primers (900 nM), 200 nM VIC labeled probe and 100–200 nM FAM labeled probe. Amplification conditions on an MJ Tetrad thermal cycler (GRI) were: 1 cycle of 50° C. for 2 min, followed by 1 cycle of 95° C. for 10 min and 40 cycles of 95° C. for 15 s and 60 to 64° C. for 1 min. Completed PCRs were read on an ABI PRISM 7700 Sequence Detector and analyzed using the Allelic Discrimination Sequence Detection Software (Applied Biosystems). Double stranded artificial templates controls were constructed using a long forward primer specific for each SNP with a long common reverse primer that overlapped the forward primer. Primers were filled-in using standard methods. We designed TaqMan primers and probes using the Primer Express Oligo Design Software v1.0 (Applied Biosystems). Probes were MGB probes designed specifically for "Taqman" Allelic Discrimination (Applied Biosystems). Primers and probes are as follows: ZNF217 Intron 4+646 forward primer: 5'CTGTTGCAGCAGAGGGCTTAG-3' (SEQ ID NO:3), ZNF217 Intron 4+646 reverse primer: 5'-CAGCAAGGAGGTAGCCACAGA-3' (SEQ ID NO:4), ZNF217 Intron 4+646 "C" probe: 5'-6FAM-ATGCCCATCTGTTACATAT-MGBNFQ-3' (SEQ ID NO:5), ZNF217 Intron 4+646 "G" probe: 5'-VIC-ATGCCCATGTGTTACATAT-MGBNFQ-3' (SEQ ID NO:6), CYP24 Intron 3–105 forward primer: 5'-TCTGATGCTAATATTCTCTGGCTATTTC-3' (SEQ ID NO:7), CYP24 Intron 3–105 reverse primer: 5'-TCCAGCTGCAACTTCAGGAAC-3' (SEQ ID NO:8), CYP24 Intron 3–105 "G" probe: 5'-6FAM-CATGATTCTCGGTGTTTGT-MGBNFQ-3' (SEQ ID NO:9), CYP24 Intron 3–105 "C" probe: 5'-VIC-CATGATTCTCAGTGTTTGT-MGBNFQ-3' (SEQ ID NO:10), CYP24 AA183 forward primer: 5'-TTTGTTTTCCTTCAACGGCTTT-3' (SEQ ID NO:11), CYP24 AA183 reverse primer: 5'-CGACCATTTGTTCAGTTCGCT-3' (SEQ ID NO:12), CYP24 AA183 "T" probe 5'-6FAM-TCTTGGCTGATTTA-MGBNFQ-3' (SEQ ID NO:13), CYP24 AA183 "C" probe 5'-VIC-TCTTGGCCGATTTA-MGBNFQ -3' (SEQ ID NO:14), CYP24 3'UTR 40 forward primer: 5'-TGCAAAATTGTTCCAGAAGCTG-3' (SEQ ID NO:15), CYP24 3'UTR 40 reverse primer: 5'-TGTAGAATGCCTTGGATCCCA-3' (SEQ ID NO:16), CYP24 3'UTR "T" probe: 5'-6FAM-CAGGGAAGTGGACTGAG-MGBNFQ-3' (SEQ ID NO:17), CYP24 3'UTR "C" probe: 5'-VIC-CAGGGAAGCGGACTGA-MGBNFQ-3' (SEQ ID NO:18), STK15 5'UTR forward primer: 5'-CAAGTCCCCTGTCGGTTCC-3' (SEQ ID NO 19), STK15 5'UTR reverse primer: 5'-CTCTAGCTGTAATAAGTAACAAGCAGTATCCT-3, (SEQ ID NO:20), STK15 5'"G" probe: 5'-6FAM-CAGCGCGTTTGCAT-MGBNFQ-3, (SEQ ID NO:21), STK15 5'UTR "C" probe: 5'-VIC-CAGCGCCTTTGCA-MGBNFQ-3, (SEQ ID NO:22), STK15 AA31 forward primer: 5'-TTCCATTCTAGGCTACAGCTCCA-3, (SEQ ID NO:23), STK15 AA31 reverse primer: 5'-CAAGACCCGCTGAGCCTG-3, (SEQ ID NO:24), STK15 AA31-"A" probe: 5'-6FAM-CTCAGCAAATTCCTTGTCAG-MGBNFQ-3, (SEQ ID NO:25), STK15 AA31-"T" probe: 5'-VIC-CTCAGCAATTTCCTTGTCAG-MGBNFQ-3, ' STK15 3'UTR (SEQ ID NO:26) for-ward primer: 5'-CTGTGCAATAACCTTCCTAGTACCTG-3, (SEQ ID NO:27), STK15 3'UTR reverse primer: 5'-ATACTTAAAAAGAATCACATACTCATTCCAA-3, (SEQ ID NO:28), STK15 3'UTR-"C" probe: 5'-6FAM-TTGGCCAAGCCTG-MGBNFQ-3, (SEQ ID NO:29), STK15 3'UTR "G" probe: 5'-VIC-TTGGCGAAGCCTG-MGBNFQ-3' (SEQ ID NO:30).

Statistical Analyses. Deviation of the genotype frequencies from those expected under Hardy-Weinberg equilibrium was assessed in the controls by Chi-squared tests. Genotype frequencies in cases and controls were compared by Chi-squared tests. The genotypic specific breast cancer risks were estimated as odds ratios with associated 95% confidence limits by unconditional logistic regression. Results are presented for the English and Finnish studies separately together with the results of a joint analysis. In the joint analysis, each study was treated as a separate stratum in the logistic regression model.

Results:

High resolution mapping of a novel skin cancer susceptibility locus (Skts13).

Figure 1A:
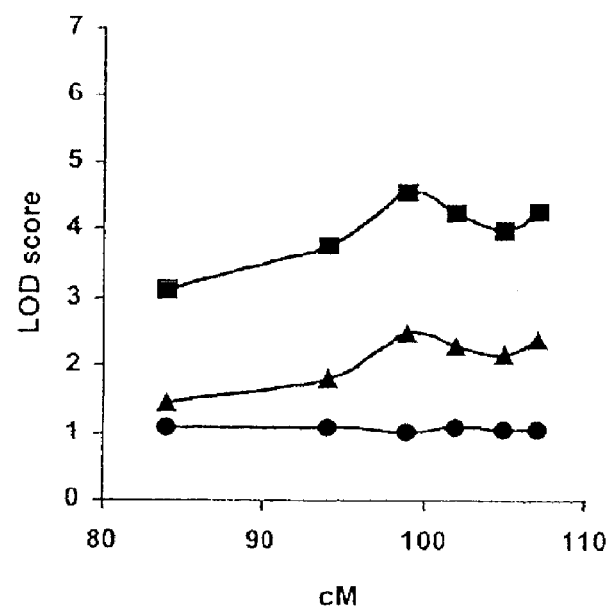
FIG. 1 shows plots of LOD score for Skts13 on distal mouse chromosome 2. Panel a plots the LOD scores of three independent F1 backcrosses, i.e. NSJ (squares), NSP (triangles), NSE (circles), are plotted. Panel b plots composite LOD score for the NSJ and NSP backcrosses. Note that only the NSP mice with haplotypes 1, 2 and 3 are included (see also Table 1).

Twelve loci have been identified by QTL analysis that control skin tumor susceptibility (Nagase, H. et al., Nature Genet., 10, 424–429 (1995); and Nagase, H., et al., Proc. Natl. Acad. Sci. USA 96, 15032–15037 (1999)), in crosses between outbred Mus spretus and inbred strains of Mus musculus. By further analysis of the same cross using more densely spaced markers than in our previous study, we identified a new skin tumor susceptibility locus on distal chromosome 2, Skts13, that confers resistance to papilloma incidence (P=3.4E–03). Two independent backcrosses, each involving over 100 animals were also carried out between inbred strains of Mus spretus (SPRET/Ei from the Jackson Laboratory) and SEG/Pas from the Institute Pasteur and the same strain of Mus musculus (NIH/Ola). Interestingly, the cross with the SPRET/Ei mice (NSJ cross) showed an even stronger linkage with papilloma resistance at this locus (P=3.7E–05), while the SEG/Pas cross (NSE) showed no significant linkage (FIG. 1a). The fact that the results with the original outbred cross involving over 300 animals was intermediate between those obtained from the two inbred crosses suggested that within the outbred colony different alleles are segregating that are homozygous for the resistance or susceptibility alleles respectively in the SPRET/Ei and SEG/Pas mice.

Information on shared haplotypes in outbred populations of humans or experimental animals can be used to refine the locations of potential disease susceptibility genes. Therefore haplotypes were constructed for distal chromosome 2 using the variation in microsatellite lengths between the spretus alleles in the outbred colony. Four different spretus haplotypes (H1 to H4) were present in these outbred mice (Table 1), and a possible association between haplotype and tumor number was investigated. The mean papilloma numbers of the different haplotypes were compared with those of mice from the same backcross that were homozygous NIH/Ola at this locus. Tumor number for each of the haplotypes H1, H2, and H3, when considered separately, differed significantly from mice that were homozygous NIH/Ola at this locus (all mice from the same cross), whereas H4 did not (H1 P=0.06, H2 P=0.04, H3 P=0.002, H4 P=0.3). Therefore, we grouped H1, H2 and H3 together. The mean papilloma number of H1, H2 and H3 combined (2.3; n=107) also differed significantly from the mean of mice that were homozygous NIH/Ola at this locus (3.6; n=113, P=1.8E–03).

Interestingly, only two small intervals appeared to be shared by H1, H2 and H3 that differed from H4, i.e. D2Mit50 at 95.5 cM, and a region from D2Mit172 to D2Jau1 at 98.5 to 100 cM. If the haplotypes of the inbred *spretus* strains are included in this analysis and an interval is identified that is shared by H1, H2, H3 and SPRET/Ei (strong linkage in NSJ cross) that differs from both H4 and SEG/Pas (no linkage in NSE cross), only part of the second region qualifies, thus refining the locus to approximately 1 cM (with the causal polymorphism predicted to map between D2Mit229 and J2Jau1).

Figure 1B:
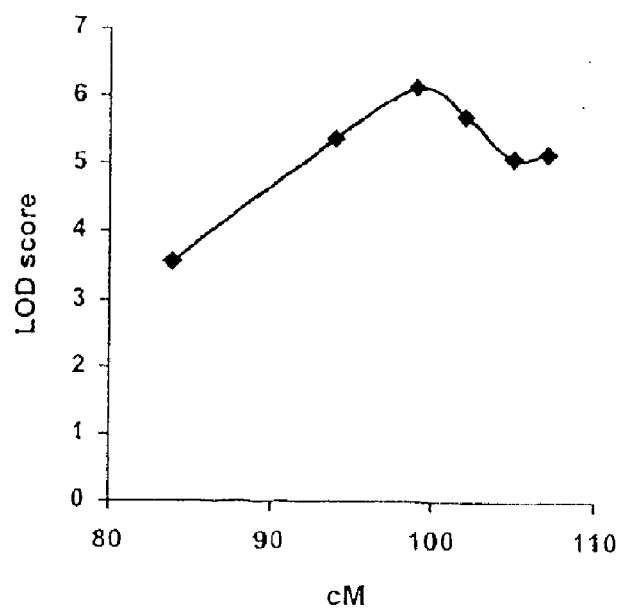

To determine the precise location of the LOD score peak, data from the NSJ backcross was combined with data from NSP mice carrying H1, H2 or H3 and the composite LOD scores were calculated. Most importantly, the 1-cM region between D2Mit229 to D2Jau1 identified by haplotyping appeared to be identical to the part of distal chromosome 2 with the highest LOD score (6.1 at 99 to 100 cM, FIG. 1b). This co-incidence of haplotyping and linkage analysis data provided strong support for the location of a susceptibility/ resistance allele within this interval. In addition, in a previous interspecific cross with *Mus spretus* mice, a hepatocellular tumor susceptibility locus, Hcs4, was mapped to distal chromosome 2, also peaking at 99 cM, suggesting that the region identified contains an important modifier affecting tumorigenesis in several model systems.

Additional evidence excluding the most telomeric end of chromosome 2 was provided by an independent study with mice that were generated by backcrossing for four generations to NIH/Ola. Papilloma numbers of mice homozygous for NIH/Ola alleles on proximal chromosome 2 but heterozygous for the most distal part (from D2Mit74 at 107 cM to the telomere) were similar to those of mice that were homozygous NIH/Ola for the entire length of chromosome 2 (data not shown).

A Physical Map of Skts13

Skts13 lies within a region of distal mouse chromosome 2 that is orthologous to a locus on human chromosome 20q13.2 showing frequent amplification in a variety of tumor types including breast, colon, and ovarian cancer (Kallioniemi, A. et al., *Proc. Natl. Acad. Sci. USA* 91, 2156–2160 (1994); Iwabuchi, H. et al., *Cancer Res.* 55, 6172–6180 (1995); and Korn, W. M. et al., *Genes, Chromosomes, and Cancer* 25, 82 (1999)). Increased 20q13.2 copy-number is observed in approximately 18% of primary breast tumors and 40% of breast cancer cell lines and is associated with aggressive tumor behavior, poor prognosis, cellular immortalization, and genomic instability. Detailed analysis of human 20q13 demonstrated the existence of two amplicons, one on 20q13.1 and another on 20q13.2, that can be either coamplified or amplified independently (Tanner, M. M. et al., *Clin. Cancer Res.* 6, 1833–1839 (2000)). Candidate genes within the amplicon on 20q13.1 are the genes PTPN1, encoding a phosphotyrosine phosphatase, and MYBL2, a gene related to the v-Myb oncogene. The distal amplicon on 20q13.2 is more frequently amplified in breast cancer and consists of at least three smaller subamplicons, each containing a putative driver gene for amplification, i.e. ZNF217 (encoding a putative Kruppel-like transcription factor), CYP24 (encoding vitamin D 24 hydroxylase), and STK15 (encoding a centrosome-associated kinase), respectively (Collins, C. et al., *Proc. Natl. Acad. Sci. USA* 95, 8703–8708 (1998); Albertson, D. G. et al., *Nature Genet.* 25, 144–146 (2000); Zhou, H. et al., *Nature Genet.* 20, 189–193 (1998); Bischoff, J. R. et al., *EMBO J.* 17, 3052–3065 (1998); and Sen, S., et al., *Oncogene* 14, 2195–2200 (1997)).

Figure 2:
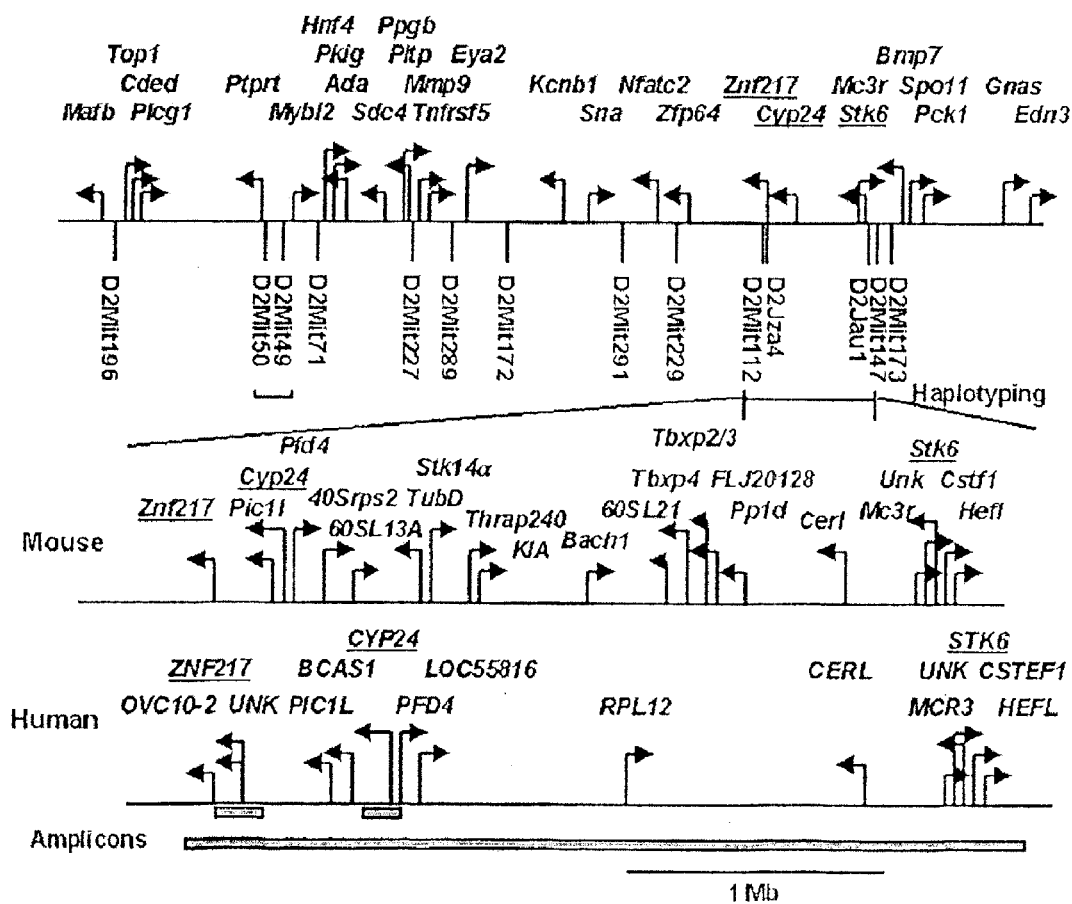
FIG. 2 shows mouse and human physical maps surrounding STK15 (STK6). Two scaffolds from the Celera database (GA_x5J8B7W6F1G and GA_x5J8B7W5RL6) were used to construct the mouse map (upper). Arrows indicate the orientation of the genes. The human map (lower) was constructed with data from the Celera database (http://www.celera.com) and the human genome project (http://www.ensembl.org). Both the intervals identified by haplotyping (in the mouse) and the (sub)amplicons at the orthologous human locus are indicated.

To identify the genes located within the region of the mouse genome defined by haplotyping, a physical map of the distal part of chromosome 2 surrounding Skts13 was constructed using the Celera database (FIG. 2). Intriguingly, the minimum amplicon on human 20q13.2 corresponds exactly to the 1-cM interval at 99 to 100 cM that we identified by haplotyping (Collins, C. et al., *Proc. Natl. Acad. Sci. USA* 95, 8703–8708 (1998); Albertson, D. G. et al., *Nature Genet.* 25, 144–146 (2000); Zhou, H. et al., *Nature Genet.* 20, 189–193 (1998); Bischoff, J. R. et al., *EMBO J.* 17, 3052–3065 (1998); Sen, S., et al., *Oncogene* 14, 2195–2200 (1997)). Moreover, the region at 95.5 cM (containing D2Mit49 and D2Mit50) maps closely to the Myb12 gene and is thus at least partly orthologous to the 20q13.1 amplicon. These results indicate that the strategy used identified two small intervals of which both human counterparts are amplified in tumors. Based on the location of the LOD score peak (FIG. 1B), mapping of the hepatocellular tumor susceptibility locus Hcs4 to 99 cM, and the high frequency of 20q13.2 amplification in tumors, we decided to focus on the region at 99 to 100 cM, orthologous to the 20q13.2 amplicon. The possibility that the interval around D2Mit49-50 contains an additional susceptibility gene(s) remains to be investigated.

Human Candidate Genes on 20q13.2

One of the problems in identification of the critical polymorphic gene within a mouse modifier locus is that most if not all of the genes within the finely mapped region will exhibit polymorphisms that segregate with the phenotypes of the parental strains. Alternative candidates within the Mom-1 colon adenoma modifier locus on chromosome 4 were eventually resolved by generating congenic mice, which allowed at least some of the candidates to be excluded (Cormier, R. T. et al., *Oncogene* 19, 3182–3192 (2000)). Rather than perform this step, the outbred human population was exploited in an attempt to find a relevant gene within this locus by association analysis. Strong linkage disequilibrium in man usually extends no more than 100 kb19. A polymorphism that shows significant association with disease risk in a population based case-control study is likely to lie very close to the causal polymorphism, defining a unique or at most a very small set of possible susceptibility genes.

At current estimates there are 15 genes mapping to the corresponding refined region of linkage in mouse (FIG. 2, International Human Genome Sequencing Consortium. *Nature* 409, 860 (2001)), 7 of which were mapped to the locus when this work was initiated (OVC10-2, ZNF217, PIC1L, BCAS1, CYP24, STK15, and MCR3). Three candidate genes, ZNF217, STK15 (also known as AURORA2, ARK1, AIK1, BTAK, STK15), and CYP24, were chosen for study because of their documented involvement in human cancer(Collins, C. et al., *Proc. Natl. Acad. Sci. USA* 95, 8703–8708 (1998); Albertson, D. G. et al., *Nature Genet.* 25, 144–146 (2000); Zhou, H. et al. *Nature Genet.* 20, 189–193 (1998); Bischoff, J. R. et al. *EMBO J.* 17, 3052–3065 (1998);

and Sen, S. et al., *Oncogene*, 14, 2195–2200 (1997)). To identify single nucleotide polymorphisms in these genes for association studies, the coding regions and intron/exon boundaries were sequenced in 12–15 controls of mixed racial ancestry (Table 3). Over thirty polymorphisms were identified, of which most were not reported in the public databases (Table 3). Six SNPs from ZNF217, CYP24, and STK15 were chosen and used for association studies based on their allele frequency (greater than 15% for the minor allele), position in gene (near a splice site, in the 5' or 3'UTR), and/or potential functional role (change of an amino acid).

A case-control sample was chosen from East Anglia of 1944 breast cancer cases and 2496 female controls from the European Prospective Investigation into Cancer (EPIC) (Riboli, E. (1992); and Day, N. et al. (1999)). A smaller population, of Finnish cases and controls, was used in an attempt to confirm positive findings and obtain a more precise risk estimate. No significant differences in genotype frequencies between cases and controls were observed for SNPs in either ZNF217 or CYP24. However, there was some evidence of a difference for the STK15 F31I polymorphism (P=0.07), with Ile homozygotes at increased risk (OR 1.42, 95% CI 1.04-1.94; Table 2). A similar trend was also observed in the Finnish series (OR 1.37, 95% CI 0.84–2.23). When data were combined, the genotype frequencies were significantly different in the cases and controls (C2=6.67, 2 d.f., p-value=0.036) with a combined Ile homozygote OR of 1.40 (95% CI of 1.07–1.82, P=0.036). These results support the conclusion that Ile31 of STK15 is a low penetrance susceptibility allele. Further studies are in progress with other populations to confirm the observed association. No significant association was observed for two other SNPs in the 5'UTR and 3'UTR of STK15 (Table 2). Although there is some linkage disequilibrium (LD) between these polymorphisms (5'UTR vs F31I: D'=0.2; 3'UTR vs F31I: D'=0.7), the STK15 Ile31 allele was in LD with a much rarer SNP in the 5'UTR (frequency 7%) and a much commoner SNP in the 3'UTR (frequency 74%) which may explain why no significant association was seen with these polymorphisms.

TABLE 1

Haplotyping of the distal part of chromosome 2

| | Location SEG/Pas | Outbred *Mus spretus* H1 | H2 | H3 | (A) H4 | Marker Inbred strains SPRET/Ei |
|---|---|---|---|---|---|---|
| D2Mit346 | 91.8 cM | A | B | B | B | C | A |
| D2Mit196 | 92 cM | A | B | B | B | C | A |
| D2Mit49 | 95.5 cM | A | A | B | C | A | D |
| D2Mit50 | 95.5 cM | A | A | A | B | C | D |
| D2Mit71 | 96 cM | A | B | B | B | C | A |
| D2Mit227 | 98 cM | A | B | B | C | A | A |
| D2Mit289 | 98 cM | A | B | B | A | B | A |
| D2Mit172 | 98.5 cM | A | A | A | B | C | D |
| D2Mit311 | 99 cM | A | A | A | B | C | A |
| D2Mit291 | 99 cM | A | A | A | B | C | B |
| D2Mit229 | 99 cM | A | A | A | B | C | A |
| D2Mit117 | 99 cM | A | A | A | B | * | B |
| *D2Jza4* | *99 cM* | *A* | *A* | *A* | *B* | * | *B* |
| D2Mit198 | 100 cM | A | A | A | B | * | B |
| D2Jau1 | 100 cM | A | A | A | B | C | A |
| D2Mit147 | 102 cM | A | B | B | B | A | B |
| D2Mit173 | 100 cM | A | B | B | B | B | A |
| D2Mit113 | 103 cM | A | B | B | B | C | B |
| D2Mit173 | 105 cM | A | B | B | B | B | B |
| Mean papilloma number | | 2.8 | 2.2 | 0.4 | 3.6 | | |
| Number of mice | | 63 | 33 | 11 | 23 | | |

Sizes of the *spretus* alleles present in the F1 backcross mice were determined for microsatellite markers spanning the entire distal region of chromosome 2. The letters A, B, C, and D refer to different alleles. Four different haplotypes (H1 to H4) appeared to be present in the outbred *Mus spretus* colony. Indicated are the number of NSP backcross mice with these haplotypes and the mean papilloma numbers for each haplotype. The gray areas refer to regions shared by H1, H2 and H3 that differ from H4. The alleles of the inbred *spretus* mice used in this study are also given for comparison. D2Jza4 refers to a CA repeat sequence within intron 1 of the Znf217 gene; D2Jau1 refers to a CA3 repeat sequence located 8.1 kb distal of the 5' end of the STK6 gene.

TABLE 2

Genotype Specific Risks for STK15 SNPs

| SNP | Genotype | Case | English Control | OR | 95% CI | p-value | Case | Finnish Control | OR | 95% CI | p-value | OR | Combined 95% CI | p-value |
|---|---|---|---|---|---|---|---|---|---|---|---|---|---|---|
| 5'UTR | CC | 1437 | 1615 | 1 | | | 446 | 418 | 1 | | | 1 | | |
| | CG | 188 | 225 | 0.94 | 0.76–1.15 | 0.95 | 37 | 33 | 1.03 | 0.63–1.67 | 0.84 | 0.95 | 0.79–1.15 | 0.79 |
| | GG | 11 | 12 | 1.03 | 0.45–2.34 | 0.94 | 1 | 0 | N/A | N/A | 0.61 | 1.12 | 0.50–2.50 | 0.64 |
| | Total | 1636 | 1852 | | | | 484 | 451 | | | | | | |
| AA31 | TT | 946 | 1281 | 1 | | | 257 | 242 | 1 | | | 1 | | |
| | AT | 511 | 706 | 0.99 | 0.86–1.14 | 0.71 | 187 | 172 | 1.03 | 0.78–1.35 | 0.84 | 0.99 | 0.87–1.12 | 0.88 |
| | AA | 86 | 82 | 1.42 | 1.04–1.94 | 0.03 | 45 | 31 | 1.37 | 0.84–2.23 | 0.21 | 1.4 | 1.07–1.82 | 0.01 |
| | Total | 1543 | 2069 | | | | 489 | 445 | | | | | | |
| 3'UTR | GG | 788 | 982 | 1 | | | 169 | 149 | 1 | | | 1 | | |
| | CG | 555 | 706 | 0.98 | 0.85–1.13 | 0.78 | 213 | 185 | 1.02 | 0.76–1.36 | 0.92 | 0.99 | 0.87–1.13 | 0.86 |
| | CC | 101 | 124 | 1.02 | 0.77–1.34 | 0.92 | 78 | 79 | 0.87 | 0.59–1.28 | 0.48 | 0.95 | 0.76–1.19 | 0.68 |
| | Total | 1444 | 1812 | | | | 462 | 413 | | | | | | |

CI= Confidence Interval
a. OR= Odds Ratios
P-values refer to OR significance levels

TABLE 3

Polymorphisms in Candidate Genes at 20q13.2

| Gene/Polymorphism | Allele | Initial Frequency | Chromosomes Tested | Database |
|---|---|---|---|---|
| ZNF217 | | | | |
| 5'UTR −130 bp | T | 94.00% | 32 | No |
| | C | 6.00% | | |
| AA133 (Silent) | T | 91.00% | 56 | No |
| | C | 8.00% | | |
| AA342 (Silent) | A | 96% | 158 | No |
| | T | 4% | | |
| AA739 (Val to Ile) | G | 97% | 60 | No |
| | A | 3% | | |
| AA889 (Asp to Gly) | A | 92% | 26 | No |
| | G | 8% | | |
| Intron 3 −8 bp | T(10) | 88% | 76 | No |
| | T(11) | 12% | | |
| Intron 4 +646 bp | C | 61% | 118 | Celera |
| | G | 39% | | |
| Intron 4 −11 bp | T | 91% | 22 | No |
| | G | 9% | | |
| 3'UTR 710 bp | A | 81.00% | 32 | dbSNP |
| | G | 19% | | |
| 3'UTR 749 bp | G | 94% | 34 | No |
| | A | 6% | | |
| CYP24 | | | | |
| Intron3 −105 | A | 48% | 122 | No |
| | G | 52% | | |
| AA156 (Arg-Trp) | C | 97% | 30 | No |
| | T | 3% | | |
| AA183 (Silent) | C | 50% | 28 | GDB |
| | T | 50% | | |
| Intron 5 +57 | A | 87% | 170 | No |
| | G | 13% | | |
| Intron 8 −70 | T | 83% | 30 | No |
| | C | 17% | | |
| AA374 (Silent) | G | 90% | 30 | No |
| | A | 10% | | |
| Intron 9 +178 | G | 83% | 30 | No |
| | A | 17% | | |
| Intron 9 −200 | C | 81% | 26 | No |
| | T | 19% | | |
| Intron 10 +26 | T | 88% | 24 | No |
| | C | 12% | | |
| Intron 10 +48 | T | 89% | 26 | dbSNP |
| | C | 11% | | |
| 3'UTR 40 bp | C | 75% | 116 | Celera |
| | T | 25% | | |
| 3'UTR 130 bp | C | 67% | 30 | Celera |
| | T | 33% | | |
| 3'UTR 705 bp | C | 83% | 24 | No |
| | G | 17% | | |
| 3'UTR 766 bp | C | 79% | 24 | No |
| | T | 21% | | |
| PIC1L | | | | |
| 3'UTR 31 bp | A | 72% | 102 | No |
| | G | 28% | | |
| 3'UTR 296 bp | G | 58% | 24 | No |
| | C | 42% | | |
| STK6 | | | | |
| 5'UTR 150 bp | C | 92% | 24 | dbSNP |
| | G | 8% | | |
| Intron 2 +62 bp | Insertion | 83% | 148 | No |
| | Deletion | 17% | | |
| AA31 (Phe to Ile) | T | 82% | 120 | 18 |
| | A | 18% | | |
| AA57 (Ile to Val) | G | 84% | 116 | DbSNP |
| | A | 16% | | |
| AA373 (Met to Val) | A | 93% | 58 | No |
| | G | 7% | | |
| 3'UTR 423 bp | G | 74% | 136 | DbSNP |
| | C | 26% | | |

EXAMPLE 2

Expression and Amplification Analysis of STK15 (STK6)

This example provides further evidence that STK15 (STK6) is a low penetrance tumor susceptibility gene by illustrating that the STK6 allele of the more tumor-prone *mus musculus* is amplified more frequently, and expressed at higher levels than the STK6 allele of the less tumor prone *mus spretus*. Furthermore, the experiments described herein identify allele-specific amplification of STK15 (STK6).

Allele Specific Expression and Allele Specific Amplification Assays. Allele specific expression and allelic specific amplification was measured using the ABI PRISM 7700 sequence detection system (Applied Biosystems). Amplification conditions and reactions were as described above, except that PCR reactions for allele specific expression (50 ml) contained 50 ng reverse transcribed RNA or 50 ng genomic DNA. Normal colon mucosal DNA and colon tumor DNA for allelic specific amplification studies was amplified by whole genome amplification prior to TaqMan® studies. PCR was performed in triplicate for each sample and experiments were repeated at least three times. CT values were normalized to the average normal genomic CT difference in each experiment. The CT value differences between the two probes for the triplicates were then averaged. The forward primer was 5'-CCC AAG AAC CAT GCT GCT TT-3' (SEQ ID NO:31); The reverse primer was 5'-GCC CAG GGT GAG GGT AGG-3' (SEQ ID NO:32); and the Taqman probes were the following: "A" Probe: 5'-VIC-AGG GAA GAT TCC ACT GCA-MGBNFQ-3' (SEQ ID NO:33); and "G" probe: 5'-6FAM-AGG GAA GGT TCC ACT GC-MGBNFQ-3' (SEQ ID NO:34).

We focused on the STK15 (STK6) gene since it was the only gene of the three tested to have a polymorphism showing strongly suggestive evidence of association with cancer risk. Expression analysis using a panel of murine skin tumor cell lines showed undetectable expression of Cyp24 (data not shown), which was therefore not investigated further. To screen for critical single nucleotide polymorphisms (SNPs) in Znf217 and STK15, both of which were expressed in the cell lines, we determined the coding sequences of these genes in NIH/Ola and SPRET/Ei. Polymorphisms in SPRET/Ei were considered potentially important if they were also present in the positive haplotypes H1, H2 and H3 but absent in H4 and SEG/Pas. In Znf217, 39 SNPs were identified of which none fitted the genetic screening criteria (data not shown). In STK6, 8 SNPs were identified that all appeared to be silent (data not shown).

Figure 3A:
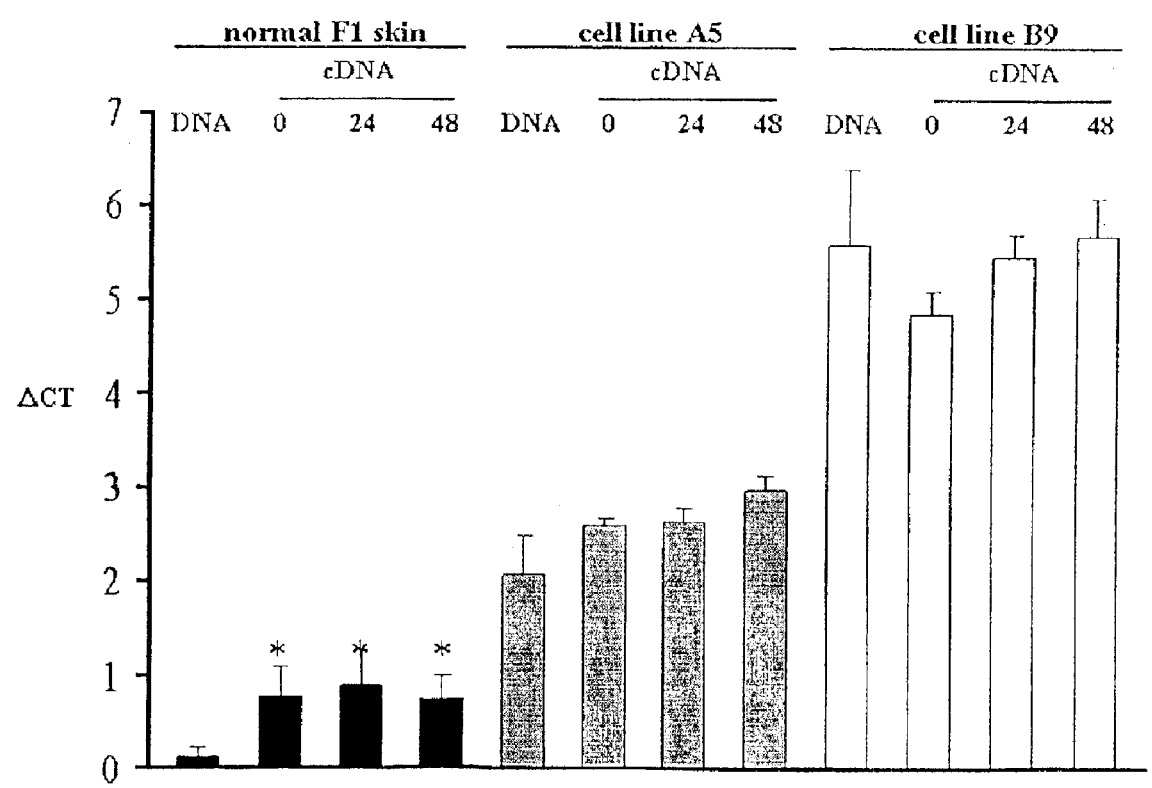
FIG. 3 shows a plot allelic expression of STK6. For Panel a, cDNA was prepared from untreated (0) and TPA-treated (24 or 48 hours) normal skin from (NIH/OlaxSPRET/Ei) F1 mice and skin tumor-derived *musculus/spretus* hybrid cell lines A5 and B9. The ratio between *musculus* and *spretus* STK6 in these samples was determined by TaqMan™ analysis using allele specific probes and is expressed as differences in CT levels (cycles) with positive DCT values indicating over-expression of *musculus* STK6 and negative DCT values of *spretus* STK6. All cDNA samples including normal skin from F1 mice over expressed the *musculus* allele of STK6 independent of TPA treatment. For comparison, the *musculus/spretus* ratio was also determined in genomic DNA. As expected, this ratio is close to 1 (DCT is approximately 0) in normal skin from F1 mice. The cell lines B9 and A5 showed clear amplification of the *musculus*
Figure 3B:
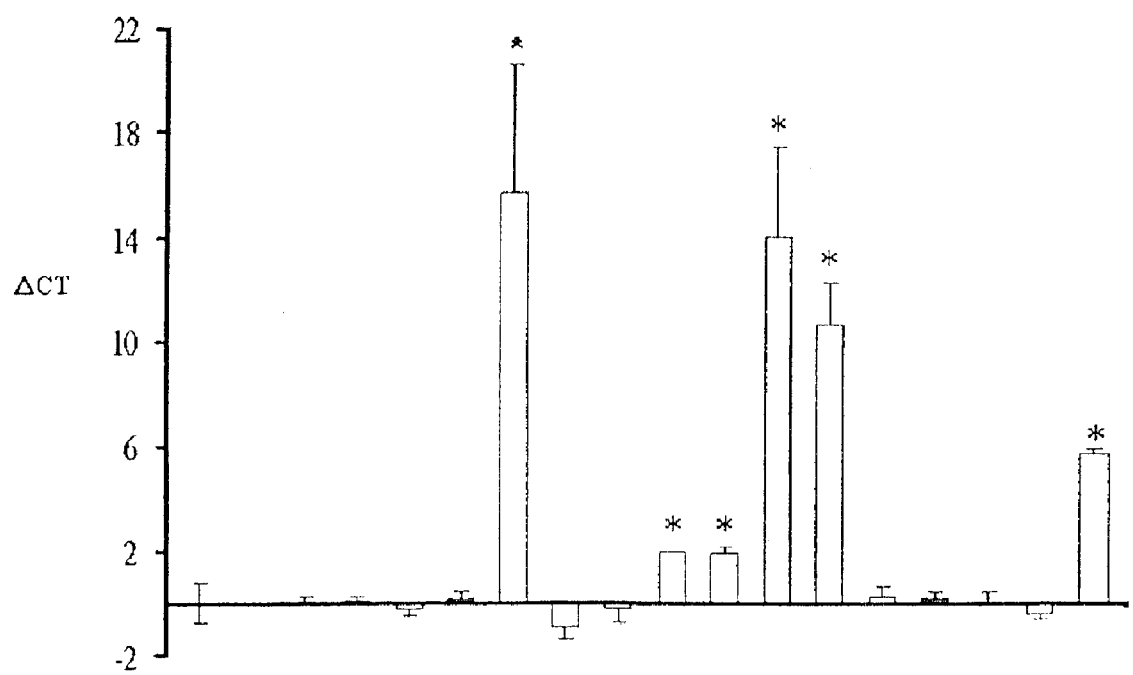
Figure 3C:
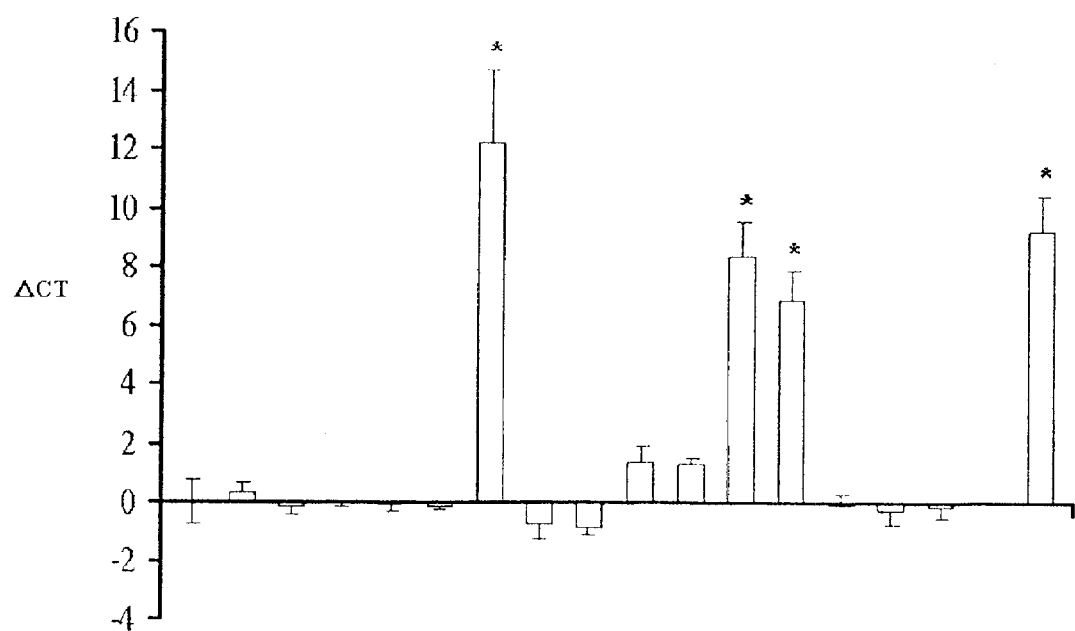

Next, we investigated possible expression differences of Znf217 and STK6 between NIH/Ola and SPRET/Ei. Allele-specific expression of these genes was determined in normal and TPA-treated skin from (NIH/Ola×SPRET/Ei) F1 mice by RT-PCR and subsequent RFLP (restriction fragment length polymorphism) analysis. Although no differences in expression of Znf217 could be detected between *musculus* and *spretus* alleles, *musculus* STK6 was expressed at significantly higher levels than *spretus* STK15 (data not shown). To confirm and quantify these results, we designed TaqMan® probes specific for intra-exon polymorphisms that distinguish between *musculus* and *spretus* alleles of STK6. Repeated TaqMan® analyses of cDNA derived from RNA from normal and TPA-treated skin indeed showed a significant small but reproducible difference in expression of approximately 0.8 CT in favor of the *musculus* STK6 allele, independent of TPA treatment (FIG. 3a). As a control, similar experiments using genomic DNA from the same F1 hybrid animals showed a 1:1 ratio by Taqman® analysis (FIG. 3a). We then examined the expression patterns in several *musculus/spretus* hybrid cell lines derived from skin tumors. The F1 hybrid cell lines B9 and A5 clearly showed 5–6 fold overexpression of the *musculus* allele of STK6, and this was associated with a similar level of amplification of the gene (FIG. 3a). From a total of 19 cell lines that were available from F1 mice, 8 significantly over expressed the *musculus* STK6 allele (DCT ranging from 1.9 to 15) (FIG. 3b), and in 5 cases, overexpression was associated with specific amplification of the *musculus* allele (FIG. 3a,c). No cases were detected of amplification and/or overexpression of the *spretus* allele. This result is statistically highly significant (p=0.0039), and lends strong support to the conclusions from the linkage data that a germline difference must exist between the *spretus* and *musculus* alleles of STK15.

In an attempt to find the causal polymorphism, approximately 5000 bp of the STK15 upstream region containing the promoter was sequenced from NIH/Ola, SPRET/Ei, one of the original outbred *spretus* mice, and mice representing each of the haplotypes H1, H2 and H4. However, no polymorphism has been identified that could explain the linkage and haplotype data. The identification of the causal mouse STK6 polymorphism might require much more extensive sequencing since control elements can be located at a considerable distance from the transcriptional start site, or within introns or 3' regulatory regions, and further studies are in progress to address this question. It can be concluded however, that there is an allele-specific difference in the regulation of STK15 that is in agreement with a role as a tumor modifier gene. Further studies will be necessary to identify the causal polymorphism and to clarify the exact mechanism of transcriptional regulation.

The STK15 gene was originally identified as a frequently amplified gene in human colon cancers. To determine if there was allele-specific amplification of the Ile31 allele STK15 in human tumors, we genotyped DNA samples from 162 individuals for whom both normal colon mucosa and colon tumor DNA was available. We chose a population of colon tumors rather than breast tumors because STK15 is amplified in approximately 50% of colon tumors, but only 12% of breast tumors (Zhou, H. et al., *Nature Genet.*, 20, 189–193 (1998) and Bischoff, J. R. et al., *EMBO J.* 17, 3052–3065 (1998)). Of the 162 normal samples typed, 48 were heterozygous for the amino acid 31 polymorphism. These 48 samples were analyzed for allele specific amplification of the AA31 polymorphism of STK15 by TaqMan analysis (FIG. 4 and data not shown). 21 samples showed no allelic imbalance between the two alleles, 4 samples showed amplification of the T (Phe) allele, and 19 samples showed amplification of the A (Ile) allele. Four samples showed differences of CTs of less than 0.6 and were scored as uncertain. These results demonstrate statistically significant allele-specific amplification of the Ile31 allele (Chi-squared test, p-value=.018), providing additional evidence for the role of the Ile31 allele in human cancer. The possibility that the results are explained by another gene in LD with Aurora is highly unlikely since LD in humans usually extends no more than 100 kb (Reich, D. E. et al., *Nature*, 411, 199–204 (2001)) and the other main candidate genes, such as ZNF217 and CYP24, are located much further away than 100 kb (FIG. 2). From LD analysis at the STK15 locus, we have specifically shown that the SNPs identified in both ZNF217 and in CYP24 are not in LD with the STK15 AA31 SNP (D'<0.1). Statistically significant allele-specific amplification of the Ile31 allele therefore provides very strong evidence that the Ile31 allele plays an important role in human cancer. The data furthermore suggest that polymorphisms in STK15 may influence susceptibility to colon cancer, and highlight the potential usefulness of allele-specific copy number or expression changes in tumors as an alternative to linkage studies in both mouse and human systems for the detection of tumor susceptibility genes.

It has been widely recognized that the next major challenge in determining the genetic basis of cancer susceptibility is the identification of the multiple low penetrance genes that modify risk within families, and contribute to individual susceptibility to sporadic cancers (Ponder, B. A. J., *Nature* 411, 336–341 (2001)). The approach disclosed herein exploits the power of mouse genetics to map low penetrance loci by linkage analysis and haplotyping. The use of outbred *Mus spretus* in crosses with inbred *Mus musculus* allowed 1s both analyses to be carried out on the same experimental data set, obviating the necessity to refine the region containing the modifier locus by traditional methods such as generation of congenic mice. This approach is applicable to the mapping of modifier genes for phenotypes induced by transgenes or knockouts, since the *spretus* alleles can generally be distinguished from most *musculus* alleles by microsatellite analysis. By combining this strategy with human population studies that exploit the low level of linkage disequilibrium in humans, we were able to refine the search to single candidate genes.

This approach has allowed the identification of what appears to be a common tumor modifier in both systems, although the mechanisms by which the gene variants modify risk may differ between mouse and human. In the human case, the polymorphism that shows a significant association lies within the coding region, but preliminary studies suggest that the kinase activity of both variants of STK15 is not substantially different (data not shown). It is therefore possible that the polymorphism affects substrate recognition, or is in linkage disequilibrium with an unknown polymorphism that increases risk. In the mouse, the polymorphism may act at the level of transcription or mRNA stability, since differences were found in the expression patterns of the parental *musculus* and *spretus* alleles in normal cells. In several tumor cell lines, increased *musculus* expression was associated with amplification of the *musculus* allele. Interestingly, the analysis of cells derived from F1 hybrid mice showed that *musculus* gene amplification could take place over quite a large region of distal mouse chromosome 2, suggesting, in line with the observation of multiple independent amplicons in the orthologous human part of chromosome 20q13.2, that several genes in this region may influence tumor development. Our conclusion that STK15 is one of the critical genes in this region is based on increased expression of the *musculus* allele in normal cells from F1 mice, consistent amplification of this allele in tumor cell lines, positive results from human association studies, and allele-specific amplification in human colon tumors. Further studies will be necessary to determine the exact functions of the polymorphisms in both mouse and human systems.

STK15 (STK6) is a member of the Aurora/Ip11p family of mitotically regulated serine/threonine kinases that are key regulators of chromosome segregation and cytokinesis (Bischoff, J. R. & Plowman, G. D., *Trends Cell Biol.* 9, 454–459 (1999). Although its exact physiological and biochemical functions are still elusive, STK15 (STK6) encodes a centrosome-associated kinase that is highly expressed at the G2 and M phase of the cell cycle (Bischoff & Plowman (1999)). A variety of primary human tumor types including 52% of colorectal, 38% of ovarian, and 12% of breast tumors show amplification of STK15. A wealth of functional data exists showing that overexpression of the normal STK15 allele leads to centrosome amplification, chromosomal instability and transformation (Tanner, M. M. et al., *Clin. Cancer Res.* 6, 1833–1839 (2000); Zhou, H. et al., *Nature Genet.* 20, 189–193 (1998); Bischoff, J. R. et al., *EMBO J.* 17, 3052–3065 (1998); Sen, S., et al., *Oncogene* 14, 2195–2200 (1997); Miyoshi, Y., et al., *Int. J. Cancer* 92, 370–373 (2001)). Immunohistochemical analyses revealed overexpression of STK15 in 94% of invasive ductal adenocarcinomas of the breast, which is intriguing since genetic instability is an early event in the development of ductal breast carcinoma (Tanaka, T. et al., *Cancer Res.* 59, 2041–2044 (1999); and Romanov, S. R. et al., *Nature* 409, 633–637 (2001)). All these findings evidently support our hypothesis that elevated expression of STK15 might modify cancer risk, perhaps by leading to aneuploidy. During mouse skin carcinogenesis, initiation by mutation of the H-ras gene is followed by trisomy of chromosomes 7 and 6 (Aldaz, C. M. et al., *Mol. Carcinog.*, 2, 22–26 (1989); Kemp, C. J. et al., *Cancer Res.* 53, 6022–6027 (1993); Bremner, R., et al., *Mol. Carcinog.* 11, 90–97 (1994)), an event that could be facilitated by increased expression of STK15.

In summary, linkage and haplotype analysis using a mouse skin model system and association studies with human breast cancer populations have provided evidence for a germline polymorphism on distal mouse chromosome 2/human chromosome 20q13 that confers increased cancer risk. One of the candidates within the region of interest, STK15, is known to cause aneuploidy and cell transformation when over expressed in human cells, and this gene is amplified in an allele-specific manner in both mouse skin and human colon tumors. Although we can not exclude the possibility that other genes in this region may also be involved, since quantitative trait loci (QTLs) frequently involve contributions from more than one gene (Balmain, A. (2002)., the combined data from these different approaches provides very strong evidence that variant alleles of STK15 (STK6) influence cancer risk in both mouse and human systems.

A cross-species strategy as described here may lead to the identification of novel genes based on the mapping of loci in mouse models. A particularly important feature that is emerging from the mouse studies is the frequency and strength of epistatic interactions between modifier loci that determine phenotypic outcome (Fijneman, R., et al., *Nature Genet*, 14, 465–467 (1996); and Nagase H., et al., *Cancer Res.* 61, 1305–1308 (2001)). It is possible that significant associations will only be detected in humans by investigating the combinations of different alleles at these interacting loci. A key goal of the Human Genome Project is to assemble a comprehensive map of SNPs that can be used for association studies (The International SNP Map Working Group. A map of human genome sequence variation containing 1.42 million single nucleotide polymorphisms. *Nature,* 409, 928–933 (2001)), but genome-wide scans for modifier genes are presently prohibitively expensive. The use of appropriate mouse models to guide the prioritizing of candidate loci and genes for testing could greatly accelerate this process, leading to significant advances in understanding the polygenic basis of cancer.

What is claimed is:

1. A method for identifying a human subject having an increased risk of developing a carcinoma, the method comprising:
   a) obtaining a nucleic acid sample from the subject; and
   b) identifying a nucleotide occurrence of a single nucleotide polymorphism (SNP) of each copy of the STK15 gene corresponding to nucleotide 457 of SEQ ID NO:1, wherein an occurrence of an adenosine residue at two or more copies of the SNP is associated with increased risk of developing a carcinoma.

2. The method of claim 1, further comprising determining whether the subject is homozygous for an adenosine residue at the SNP.

3. The method of claim 2, wherein the human subject is of English or Finnish ancestry.

4. The method of claim 2, wherein the carcinoma is colon cancer, breast cancer, or prostate cancer.

5. The method of claim 2, wherein the cancer is breast cancer.

6. A method for determining cancer susceptibility of a human subject, the method comprising determining in a nucleic acid sample from the subject, the number of STK15 Ile31 alleles of the subject, wherein greater than two STK15 Ile31 alleles is indicative of an increased susceptibility to cancer, thereby determining cancer susceptibility.

7. The method of claim 6, wherein the sample comprises an isolated cell from the subject.

8. The method of claim 7, wherein the isolated cell is from a biopsy.

9. The method of claim 8, wherein the biopsy is from breast, colon, or prostate tissue.

10. The method of claim 9, wherein the biopsy is from breast tissue.

11. A method for identifying a human subject having an increased risk of developing a carcinoma, the method comprising:

a) obtaining a nucleic acid sample from the subject; and b) identifying a nucleotide occurrence of a single nucleotide polymorphism (SNP) of each copy of the STK15 gene corresponding to nucleotide 457 of SEQ ID NO:1, wherein an occurrence of an adenosine residue at two or more copies of the SNP is associated with increased risk of developing a carcinoma, and wherein the carcinoma is selected from the group consisting of colon, breast, and prostate carcinoma.

12. A method for identifying a human subject having an increased risk of developing a carcinoma, the method comprising:

a) obtaining a nucleic acid sample from the subject;

b) detecting allele-specific amplification of an STK15 allele of a human subject, wherein greater than two STK15 Ile31 alleles is indicative of the allele-specific amplification; and c) identifying a nucleotide occurrence of a single nucleotide polymorphism (SNP) of each copy of the STK15 gene corresponding to nucleotide 457 of SEQ ID NO:1, wherein an occurrence of an adenosine residue at two or more copies of the SNP is associated with increased risk of developing a carcinoma.

13. The method of claim 1, 11 or 12, wherein the sample comprises an isolated cell of the human subject.

14. The method of claim 13, wherein the isolated cell is from a biopsy.

15. The method of claim 14, wherein the biopsy is from breast tissue, prostate tissue, or colon tissue.

16. The method of claim 15, wherein the biopsy is from breast tissue.

* * * * *